United States Patent
Bentsen et al.

(12)

(10) Patent No.: US 6,664,111 B2
(45) Date of Patent: Dec. 16, 2003

(54) FLUORESCENCE BASED OXYGEN SENSOR SYSTEMS

(75) Inventors: James G. Bentsen, North St. Paul, MN (US); Ralph R. Roberts, Cottage Grove, MN (US); Orlin B. Knudson, Vadnais Heights, MN (US); Daniel Alvarez, Jr., San Diego, CA (US); Michael J. Rude, Minnetonka, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 68 days.

(21) Appl. No.: 09/935,183

(22) Filed: Aug. 22, 2001

(65) Prior Publication Data

US 2003/0099574 A1 May 29, 2003

(51) Int. Cl.$^7$ .............................................. G01N 21/64
(52) U.S. Cl. ........................ 436/68; 436/136; 436/138; 436/172; 422/82.07; 422/82.08; 422/91
(58) Field of Search .......................... 422/82.07, 82.08, 422/82.11, 91; 436/172, 136, 138, 68

(56) References Cited

U.S. PATENT DOCUMENTS

| | | | |
|---|---|---|---|
| RE31,879 E | * | 5/1985 | Lubbers et al. |
| 4,640,820 A | * | 2/1987 | Cooper |
| 4,745,076 A | * | 5/1988 | Muller et al. |
| 4,830,013 A | * | 5/1989 | Maxwell |
| 4,849,172 A | * | 7/1989 | Yafuso et al. |
| 5,012,809 A | | 5/1991 | Shulze |
| 5,030,420 A | * | 7/1991 | Bacon et al. |
| 5,070,158 A | * | 12/1991 | Halloway et al. |
| 5,128,102 A | * | 7/1992 | Kaneko et al. |
| 5,196,347 A | * | 3/1993 | Kaneko et al. |
| 5,278,043 A | * | 1/1994 | Bannwarth et al. |
| 5,409,666 A | * | 4/1995 | Nagel et al. |
| 5,462,879 A | * | 10/1995 | Bentsen |
| 5,508,509 A | * | 4/1996 | Yafuso et al. |
| 5,518,694 A | | 5/1996 | Bentsen .................... 422/82.08 |
| 5,580,527 A | * | 12/1996 | Bell et al. |
| 5,607,645 A | | 3/1997 | Bentsen et al. ........... 422/82.07 |
| 5,766,952 A | * | 6/1998 | Mann et al. .................... 436/2 |
| 5,863,460 A | * | 1/1999 | Slovacek et al. |
| 5,882,936 A | | 3/1999 | Bentsen et al. ................ 436/68 |
| 5,958,782 A | | 9/1999 | Bentsen et al. ................ 436/79 |
| 6,009,339 A | | 12/1999 | Bentsen et al. .............. 600/322 |
| 6,063,637 A | * | 5/2000 | Arnold et al. ................. 436/94 |
| 6,214,628 B1 | * | 4/2001 | Lakowicz et al. ........... 436/518 |
| 6,468,741 B1 | * | 10/2002 | Massey et al. .................. 435/6 |

FOREIGN PATENT DOCUMENTS

| | | | |
|---|---|---|---|
| CA | 2227309 | * | 7/1999 |
| EP | 0 283 206 A2 | | 9/1988 |
| EP | 0 309 214 A2 | | 3/1989 |
| EP | 0 340 605 A2 | | 11/1989 |
| EP | 1 097 980 A2 | | 5/2001 |
| WO | 99/23476 | * | 5/1999 |

OTHER PUBLICATIONS

Article: Holst et al., "O$_2$–Flux–Optode for Medical Application," *Advances in Fluorescence Sensing Technology*, SPIE vol. 1885, 1993, pp. 216–227.
Article: Hauser et al., "All Solid–State Instrument for Fluorescence–Based Fibre–Optic Chemical Sensors," *Analyst*, vol. 118, Aug., 1993, pp. 991–995.
Article: Hauser et al., "A Solid–State Instrument for Fluorescence Chemical Sensors Using a Blue Light–Emitting Diode of High Intensity," *Meas. Sci. Technol*, vol. 6, 1995, pp. 1081–1085.
Article: Bannwarth et al., "187. Energy Transfer from a Lumazine (=Pteridine–2,4(1$H$,3$H$)–dione) Chromophore to Bathophenanthroline–Ruthenium(II) Complexes During Hybridization Processes of DNA," *Helvetica Chimica Acta*, vol. 74, 1991, pp. 2000–2008.
Article: Bannwarth et al., "A Simple Specific Labelling for Oligonucleotides by Bathophenanthroline–Ru$^{II}$ Complexes as Nonradioactive Label Molecules," *Tetrahedron Letters*, vol. 30, No. 12, 1989, pp. 1513–1516.
Article: MacCraith et al., "Light–Emitting–Diode–Based Oxygen Sensing Using Evanescent Wave Excitation of a Dye–Doped Sol–Gel Coating," *Optical Engineering*, vol. 33, No. 12, Dec., 1994, pp. 3861–3866.
"Oxygen–Sensitive Luminescent Materials Based on Silicone–Soluble Ruthenium Diimine Complexes" by Klimant, et al., *Analytical Chemistry*, vol. 67, No. 18, Sep. 15, 1995, pp. 3160–3166.*
"The preparation of a sol–gel glass oxygen sensor incorporating a covalently bound fluorescent dye" by Malins, et al., *Anal. Commun.*, 199, 36, pp. 3–4.*
"Energy Transfer for a Lumazine (= Pteridine–2,4(1$H$, 3$H$)–dione) Chromophore to Bathophenanthroline ruthenium(II) Complexes during Hybridization Processes of DNA" by Bannwarth, et al.,, *Helvetica Chimic Acta*, vol. 74 (1991), pp. 2000–2008.*

* cited by examiner

Primary Examiner—Jeffrey Snay
(74) Attorney, Agent, or Firm—Jean A. Lown

(57) ABSTRACT

Sensing elements, sensor systems and methods for determining the concentration of oxygen and oxygen-related analytes in a medium are provided. The sensing element comprises a solid polymeric matrix material that is permeable to oxygen or an oxygen related analyte and an indicator that is covalently bonded to the solid polymeric matrix material. The indicator is a luminescent platinum group metal polyaromatic chelate complex capable of having its luminescence quenched by the presence of oxygen. The polyaromatic complex comprises three ligands, at least one of which is a bidentate diphenylphenanthroline. The polyaromatic complex is distributed substantially homogenously throughout the matrix material and is covalently bonded to the matrix material via a linker arm. The linker arm is attached to a phenyl group of a diphenylphenanthroline ligand and to the backbone of the polymeric matrix material. The sensor systems comprise the present sensing element, an excitation assembly, a detector assembly, and a processor assembly.

21 Claims, 15 Drawing Sheets

Solid Crosslinked Polysiloxane Matrix With Indicator Covalently Bonded To The Matrix

FLUORESCENCE BASED OXYGEN SENSOR SYSTEMS

FIELD OF THE INVENTIONS

This invention broadly relates to devices for sensing and determining the concentration of oxygen or an oxygen-related analyte in a medium. More specifically, this invention relates to sensing elements for sensing and sensor systems for determining blood or tissue oxygen concentrations.

BACKGROUND OF THE INVENTION

Oftentimes during surgical procedures, a number of blood analytes are monitored in real time. For example, during open-heart surgery, the surgeon and other members of the surgical team often monitor blood pH, as well as the concentration of various blood gases, such as $O_2$ and $CO_2$. It is also of interest to monitor these analytes in patients for extended periods of time before or after surgery. Furthermore, it is oftentimes desirable to monitor these analytes in critically ill patients in an intensive care unit. It may also be desirable to monitor other blood analytes, such as glucose, in critically ill patients.

Because of their unique properties, fluorescence-based sensing elements have been employed in sensor systems designed for real time monitoring of blood analytes including pH, $CO_2$, $O_2$ and $K^+$. The sensing element comprises a sensor film and a substrate for holding the sensor film and bringing it into contact with the patient's blood. Typically, the sensor film comprises a fluorescent substance that is distributed in a polymeric matrix that is permeable to the analyte of interest (e.g. $O_2$ and $CO_2$ sensors). Alternatively, the fluorescent substance is anchored to a polymeric film that is contacted with the analyte of interest (e.g. pH and $K^+$ sensors).

For in vivo applications, the sensor film may be disposed on the tip of an optical fiber and then inserted into an arterial catheter or into a needle for insertion into the tissue of the patient, as disclosed in Lubbers et al U.S. Pat. No. Re 31,879, and Maxwell U.S. Pat. No. 4,830,013. For ex vivo and extracorporeal applications, the sensor film may be disposed on a carrier disk and incorporated into a disposable flow through cassette, which is then placed in an arterial line circuit or an extracorporeal blood loop as shown in Cooper U.S. Pat. No. 4,640,820. Each of these patents is incorporated by reference in its entirety herein.

When exposed to light at a proper wavelength, the fluorescent substances (referred to hereinafter as "fluorophores") absorb energy and are driven from their ground state energy level into an excited state energy level. Fluorophores are unstable in their excited states and fluoresce (radiative decay) or give off thermal energy (non-radiative decay) as they return to their ground state. The fluorescence intensity, I, represents the intensity of the emission given off by the fluorophore as it returns to the ground state. The fluorescence lifetime, $\tau$, represents the average amount of time the fluorophore remains in its excited state prior to returning to the ground state.

Fluorescence based oxygen sensing elements work on the principle that oxygen molecules can collisionally quench the excited state of a fluorophore. When the fluorophore is excited in the presence of oxygen molecules, collisional interactions between the excited state and the oxygen molecule introduce a new mechanism for non-radiative decay, resulting in a decrease in both the fluorescence intensity and the excited state lifetime. Thus, blood gas monitoring systems which employ fluorescence based oxygen sensing elements have been designed to monitor oxygen-related changes in fluorescence intensity or excited state lifetime of the fluorophore.

The relationship between the fluorescence intensities and lifetimes in the absence ($I_o$, $\tau_o$) and presence ($I$, $\tau$) of oxygen is described by the Stern-Volmer equation:

$$\frac{I_0}{I} = \frac{\tau_0}{\tau} \qquad \text{Equation 1}$$
$$= \frac{k_q[O_2]}{k_{em} + k_{nro}}$$
$$= 1 + k_q \tau_0 [O_2]$$
$$= 1 + a k_q \tau_0 pO_2$$
$$= 1 + K_{SV} pO_2$$

where $[O_2]$ is the concentration of oxygen in the sensing element; $pO_2$ is the partial pressure of oxygen in the medium being sensed; a is the solubility constant for oxygen in the sensing element which equals $[O_2]/pO_2$; $k_q$ is the bimolecular quenching constant in the sensing element; $k_{em}$ represents the rate constant for radiative decay; $k_{nro}$ represents the rate constant for non-radiative decay in the absence of oxygen; and $K_{SV}$ is the Stern-Volmer quenching constant.

Relative fluorescence intensities ($I_o/I$) or relative fluorescence lifetimes $\tau_o/\tau$ are measured experimentally. Ideally, a plot of $I_o/I$ or $\tau_o/\tau$ against $pO_2$ should give a straight line with a slope of $K_{SV}=ak_q\tau_o$ and an intercept of unity. A calibration curve can be made of intensity versus concentration, and from this the concentration of the quenching species in the medium can be determined.

When a disposable flow-through cassette containing a sensor disk is clipped into the optics head of a blood gas-monitoring device, there are several factors that can lead to variability in the intensity of the fluorescent return signal that is given off by the sensing element and detected by the sensor system detector. Similarly, when a fiber optic probe having a sensor film at the distal end of the fiber is inserted into an arterial catheter or into tissue, there are several factors that can lead to variability in the intensity of the fluorescent return signal. In both configurations, these sources of variability include optical coupling efficiencies throughout the optical train, optical coupling to the cassette or fiber optic probe, lamp intensity, concentration of the fluorophore in the sensing element, and thickness of the sensing element. Even after the sensor system has been calibrated, return signal intensities can drift as a result of fiber bending, fluctuations in lamp intensity, temperature dependent changes in optical coupling efficiencies or the detection electronics, and photo-bleaching of the fluorophore. The effects of fiber bending and photo-bleaching are particularly pronounced in fiber optic probes.

A well recognized advantage of using fluorescence lifetime to determine oxygen concentration is that fluorescence lifetime is insensitive to variations in sensor film thickness, optical coupling efficiencies, fiber bending, and fluctuations in lamp intensity. The two most common techniques for measuring fluorescence lifetimes are the pulse method and the phase modulation method. In the pulse method, the fluorophore is excited by a brief pulse of light, and the decay of fluorescence is determined. In the phase modulation method, the fluorophore is excited by a light beam that is preferably sinusoidally amplitude modulated at a radial frequency $\omega=2\pi f$, where f is the frequency in cycles per second. The fluorescence emission from the fluorophore is a forced response to this excitation signal, and is therefore amplitude modulated at the same radial frequency ω as the excitation signal. However, because of the finite lifetime of the fluorophore in the excited state, the emission is phase shifted by an angle θ with respect to the excitation signal. Furthermore, the amplitude or intensity of the emission is less modulated (demodulated) by an amount m with respect to the excitation signal. The lifetime of the fluorophore can be calculated in a known manner from measurements of the phase shift (tan θ=ωτ) and the demodulation factor (m=(1+ω²τ²)⁻¹/²).

By measuring the phase shift, one can determine the fluorescence lifetime and therefore the analyte concentration. The Stern-Volmer slope is determined by measuring the phase shift and plotting the equation $$\frac{\tau_0}{\tau} = \frac{\tan\theta_0}{\tan\theta} = 1 + K_{SV} pO_2 \qquad \text{Equation 2}$$

This approach still requires measurement of a reference signal from the light source or from the driver electronics, and this reference signal must be used to correct for phase drift in the detection electronics. However, it is not necessary to send the reference signal through the sensing element since the measured phase shift is independent of optical coupling losses, fiber bending, variations in dye concentration or changes in light source amplitude.

Regardless of the method used to determine the lifetimes or intensity, the slope of the resulting Stern-Volmer calibration plots will necessarily depend on the value of $\tau_o$. Measured values for $\tau_o$ generally vary from sensing element to sensing element as a result of self-quenching and micro-heterogeneities of the fluorophore in the sensor films. Therefore, each sensing element must be individually calibrated using a two-point calibration method.

A procedure outlined in Bentsen U.S. Pat. No. 5,403,746 successfully addresses the two-point calibration issues for a flow-through cassette comprising intensity based sensing elements for pH, $CO_2$ and $O_2$. This configuration and procedure is commonly employed for extracorporeal blood gas sensing systems used during open heart surgery. This procedure is lengthy (30 min) and involves exposing the cassette to a buffer solution that is alternately exposed to two different calibration gas mixtures having different partial pressures of oxygen and carbon dioxide. The two calibrants will typically have known analyte concentrations, one close to the maximum, and the other close to the minimum concentrations of the range over which measurements are to be taken. By alternately exposing the sensing element to the two calibrants, the slope and intercept of a calibration plot may be determined so that the sensor system can accurately measure unknown concentration of blood analytes. Two point calibration involves adjusting the slope and intercept of the calibration data, as represented by the lookup table data or mathematical equation stored in memory of the sensor processor, until the relationship characterized by the data extends through the points corresponding to those of the known calibrants. A similar procedure can be applied to the calibration of single fiber sensing elements incorporated within a protective needle or inserted into an arterial catheter as taught in Maxwell U.S. Pat. No. 4,830,013.

In bedside applications, it is desirable to monitor blood gases consistently over an extended period of time. For example, it is desired to leave the sensing element in the a-line circuit for up to 72 hrs, the standard in-dwell time for an arterial catheter. Unfortunately, current sensor systems drift substantially over this period of time and require recalibration. Since two point calibration procedures require the sensing element to be exposed to two calibrants, it is necessary to remove the current sensing elements from contact with the patient's blood. However, this is not an acceptable procedure in most clinical situations since it can compromise the patient by, for example, increasing the risk of infection.

To address intensity drift in current sensing systems, several referencing schemes have been taught in the art. One commonly practiced approach is to incorporate a fluorescence decay constant that corrects for drift resulting from photo-degradation. This approach is used in correcting for drift in the potassium sensor system taught in Bentsen U.S. Pat. No. 5,958,782 and for correcting drift in the oxygen sensor system taught in Nagel U.S. Pat. No. 5,409,666, both incorporated commercially as part of the LED based sensor system taught in Bentsen U.S. Pat. No. 6,009,339. Each of these patents is incorporated in its entirety herein. Such an approach is insufficient for single fiber sensing elements where photodegradation can be more dramatic (as much as 40% declined in intensity) than in the cassette format and where intensity fluctuations associated with fiber bending are also more pronounced (as much as 60% fluctuations in intensity).

Surgical and clinical environments impose stringent constraints for precision and drift of blood oxygen sensor systems as shown below:

| | Clinical Requirements | | |
|---|---|---|---|
| Range | arterial | precision | drift |
| $pO_2$ (mm Hg) 40–180 | 100 | ±2.5 | ±6 |

To achieve such precision, the Stern-Volmer quenching constant $K_{SV}$ for an oxygen sensing system is preferably between 0.006 mm⁻¹ ($I_o/I_{air}$=2) and 0.05 mm⁻¹ ($I_o/I_{air}$=9), more preferably between 0.0075 mm⁻¹ and 0.02 mm⁻¹ ($I_o/I_{air}$=4.2), and most preferably, between 0.009 mm⁻¹ and 0.015 mm⁻¹. As discussed by Wolfbeis in *Fiber Optic Chemical Sensors and Biosensors, Vol II*, CRC Press 1991 and taught by Mauze in U.S. Pat. No. 5,057,277, when using intensity or lifetime measurements to determine analyte concentration, too large a Stern-Volmer quenching constant can be undesirable. In particular, when the quenching constant is too large, relatively large changes in lifetime or intensity values occur over a narrow range of analyte concentrations. At larger analyte concentrations of interest, analyte dependent changes in the fluorescence intensity and lifetime become undesirably small. These considerations are especially problematic in the proper design of a sensor system for monitoring oxygen partial pressure in blood, where accuracy is desired over the range of $pO_2$=40–120 mm Hg, more preferably over the range of 40–180 mm Hg.

Accordingly, for use in the bedside market, there is a need for oxygen sensor systems having calibration plots with slopes or slopes and intercepts that are insensitive to drift and instability caused by variations in fluorescence lifetime, and that can operate within the range required in the clinical environment while satisfying the above specifications for drift and precision for a period of up to 72 hours. There is also a need for oxygen sensor systems that can support rapid (under 5 minute) calibration for $pO_2$. There is also a need for oxygen sensing elements which are capable of being incorporated into a flow-through cassette based sensor system that is compact and light weight. Oxygen sensing elements which avoid leaching out of the fluorescent indicator into the body fluid or tissue are especially desirable.

SUMMARY OF THE INVENTION

The present invention provides sensor systems and methods for determining the concentration of oxygen and oxygen-related analytes in a medium, particularly an aqueous-based medium such as blood or body tissue. In one broad aspect, the present sensor systems comprise a sensing element, an excitation assembly, a detector assembly, and a processor assembly, wherein the sensing element comprises a solid polymeric matrix material that is permeable to oxygen or an oxygen related analyte and an indicator that is covalently bonded to the solid polymeric matrix material. The indicator is a luminescent platinum group metal polyaromatic chelate complex capable of having its luminescence quenched by the presence of oxygen. Platinum Group metals are Group VIIIA in the periodic table. The polyaromatic complex comprises three ligands, at least one of which is a bidentate diphenylphenanthroline. The polyaromatic complex is distributed substantially homogenously throughout the matrix material and is covalently bonded to the matrix material via a linker arm. The linker arm is attached to a phenyl group of a diphenylphenanthroline ligand and to the backbone of the polymeric matrix material.

In a particularly useful embodiment, the complex has the formula.

$$M^+L_1L_2L_3$$

wherein $M^+$ is $Ru^{2+}$, $Os^{2+}$, $Ir^{3+}$, or $Rh^{3+}$. The ligands $L_1$ and $L_2$ are ide and represent an optionally substituted bidentate phenanthroline or diphenylphenanthroline ligand or an optionally substituted cyclometallated bidentate phenylpyridine ligand or a benzo[h]quinoline ligand. The ligand $L_3$ is a bidentate diphenylphenanthroline ligand substituted by a linker arm which covalently links the metal complex to the matrix material. The linker arm comprises a group selected from the group consisting of a covalent bond, O, C(O)O, an optionally substituted methylene group, an optionally substituted carbon chain comprising 2–20 carbon atoms, and combinations thereof. The carbon chain optionally comprises one or more of the following moieties or combinations thereof: an oxygen atom, a nitrogen atom, a sulfur atom, a silicon atom, a heterocyclic group, and an aryl group. Advantageously, in such a sensing element, the indicator is homogeneously distributed throughout the solid polymeric matrix, a feature that results in linear and reproducible calibration plots.

Any suitable polymeric matrix material may be employed in the sensing element, provided that it functions as described herein. The matrix material, or the precursor thereof, should preferably be such as to chemically react with the linker arm of the indicator and produce a sensing element with a covalently bonded indicator.

Although various polymers can be employed as the matrix material, it is preferred that the matrix material be a silicone-based polymer. Particularly useful polymeric matrix materials include those based on addition cure silicone polymers. If a silicone-based polymer is employed in the matrix material, it may include polymers derived from precursors including vinyl terminated polysiloxanes and polyalkyl (aryl)hydrosiloxanes. Such polyalkyl(aryl)hydrosiloxanes include, but are not limited to, those having the formula

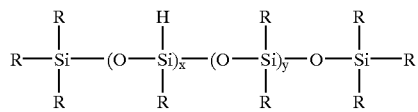

where each of x and y is independently an integer in the range of 1 to about 500 and R is independently selected from the group consisting of H, alkyl, a substituted alkyl, and a phenyl. Such vinyl terminated polysiloxanes have the formula

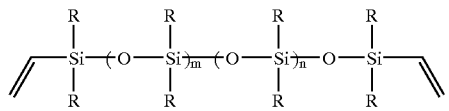

where the sum of m and n is in the range of 100–500 and R is independently selected from the group consisting of alkyl, a substituted alkyl, and a phenyl. Preferably, the silicone-based matrix is free from acids and amines that can leach from the sensing element and change its performance. For sensing oxygen concentrations that are found in blood, it is preferred that a major portion of the R groups are methyl groups. Preferably, the linker arm of the complex is attached to the silicone based polymer by a siloxane or silane linkage.

We have unexpectedly found that the combination of the functionalized indicators having $L_3$ as a bidentate diphenylphenathroline ligand substituted with a linker arm and silicone based matrix materials as described above give rise to oxygen sensing elements wherein the indicator is well dispersed and covalently attached such that the calibration slopes are highly reproducible. Sensor compositions and sensing elements made with these materials overcome several problems associated with ruthenium based oxygen sensing elements of the prior art. In particular, compositions of the extant invention give rise to sensing elements that exhibit long fluorescence lifetimes, in excess of 1 $\mu$sec. Furthermore, aggregation of the indicator is minimized, giving rise to substantially linear Stern-Volmer slopes that are consistently greater than 0.009 $mm^{-1}$ and substantially uniform over the range of oxygen partial pressures of 40–180 mm Hg. In addition, the Stern-Volmer slope can be reproducibly controlled through selection of the ratio of methyl to phenyl substituents in the siloxane polymer.

In one preferred embodiment, the solid polymeric matrix material is a dimethylsiloxane polymer or a phenylmethylsiloxane polymer which is permeable to oxygen and the indicator is a luminescent platinum group metal complex comprising at least one bidentate diphenylphenanthroline ligand having a linker arm that covalently attaches to the polymer backbone. The emission from the complex in this matrix is characterized by a bimolecular quenching rate constant $k_q$ for quenching by oxygen and by one or more fluorescence lifetimes $\tau_o$ above a lowest lifetime $\tau_{oL}$=1 $\mu$sec in the absence of oxygen, such that the Stern-Volmer quenching constant $K_{SV}$ is greater than 0.006 $mm^{-1}$ ($I_o/I_{air}$=2), more preferably greater than 0.0075 $mm^{-1}$, most preferably greater than 0.009 $mm^{-1}$, and substantially uniform over the range of oxygen partial pressures of 40–180 mm Hg.

The excitation assembly of the sensor system is positioned and adapted to provide an excitation signal to the sensing element. The excitation assembly comprises a light source that is preferably selected from the group consisting of light emitting diodes, laser diodes, frequency doubled laser diodes, and solid state light sources. The detector assembly is positioned and adapted to detect the analyte dependent signal from the sensing element and to provide a corresponding electrical signal that can be analyzed by the processor assembly.

A processor assembly is in communication with the detector assembly. The processor assembly includes memory to store information for characterizing a calibration relationship between analyte concentration and a concentration dependent parameter. The processor assembly processes the detected signals to derive the concentration dependent parameter, and provides output signals representative of analyte concentration as a function of the derived concentration dependent parameter and the stored information.

In a number of particularly useful embodiments, referred to hereinafter as "phase modulation sensors", the sensor system is configured for phase-modulation detection. In phase modulation sensor systems, the signal emitted from the sensing element is intensity modulated, preferably sine wave modulated. This may be done, for example, by exposing the sensing element to an intensity modulated excitation signal or signals. The detector assembly is adapted to sample separately the modulated excitation signal and the modulated signal emitted from the sensing element.

In a first embodiment of the phase modulation sensors, the processor assembly is adapted to determine the extent of the phase shift between the modulated excitation signal and the modulated emission signal. The extent of this phase shift is dependent on the concentration of the analyte in the medium.

In a second embodiment of the phase modulation sensors, the processor assembly is adapted to determine the magnitude of the ratio of demodulation between the modulated excitation signal and the modulated emission signal. The extent of this ratio of demodulation is dependent on the concentration of the analyte in the medium.

In a third embodiment of the phase modulation sensors, the processor assembly is adapted to determine the magnitude of the extent of the phase shift between the modulated excitation signal and the modulated emission signal. The intensity modulated excitation signal is adjusted in frequency so as to maintain a fixed phase shift difference between the modulated excitation signal and the modulated emission signal. The excitation frequency necessary to maintain a fixed phase shift between the modulated excitation and emission signals is dependent on the concentration of the analyte in the medium.

Preferably the excitation assembly, detection assembly, and processor assembly of the phase modulation sensor system are configured to operate at one or more modulation frequencies not to exceed 1 MHz, more preferably not to exceed 500 kHz, and most preferably, not to exceed 200 kHz, such that the sensor system can operate sufficiently within the condition $[(k_q[O_2])^2+\omega^2]\tau_o^2 >> 1+2k_q\tau_o[O_2]$, where $[O_2]$ is the concentration of the oxygen in the sensing element. $[O_2]$ can be estimated by the product $apO_2$. This allows the slope of the relationship between the concentration dependent parameter and analyte concentration to be independent of $\tau_o$ variability for all analyte concentration within the operating range and for all lifetimes $\tau_o$ greater than $\tau_{oL}=1$ μsec. Preferably, the sensing element and the excitation signal are configured so as to provide an operating condition where the ratio $[(k_q[O_2])^2+\omega^2]\tau_o^2/(1+2k_q\tau_o[O_2])$ exceeds 4, more preferably 6, and most preferably 10. Under these conditions, a constant calibration slope can be achieved and a rapid-single point calibration of the sensor is possible.

A still further broad aspect of the present invention is the provision of a sensor composition and sensing elements useful for sensing the concentration of an oxygen-related analyte in an medium. The present invention also relates to methods of making the sensor composition and methods of using the sensor systems of the present invention to determine blood oxygen levels in patients.

The present sensor systems provide accurate, reliable and reproducible oxygen concentration determinations over the oxygen concentration ranges normally found in human blood. In addition, the present sensor systems provide oxygen concentration determinations that are relatively drift free over a 72 hour period of time. The sensing elements of the present invention further can be manufactured to provide a reproducible calibration slope such that a rapid one-point calibration of the sensing element can be achieved.

These and other aspects and advantages of the present invention are set forth in the following detailed description and claims, particularly when considered in conjunction with the accompanying drawings.

DETAILED DESCRIPTION OF THE INVENTION

Figure 1A:
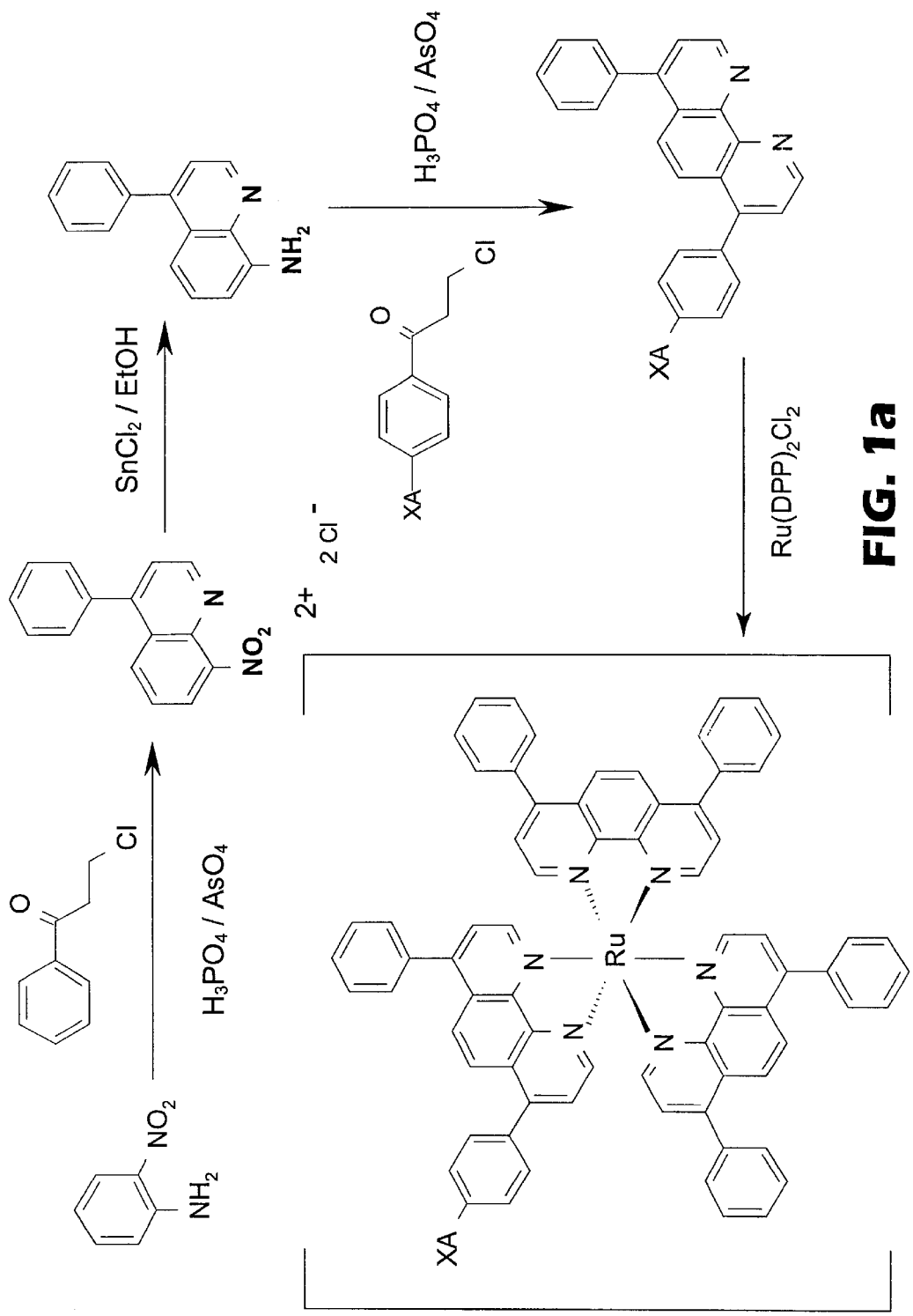
FIG. 1a is a synthetic scheme for making a functionalized indicator according to the present invention.

As used herein the term, "indicator", refers to a substance that provides a fluorescence signal in response to an excitation signal.

As used herein the term "sensor composition" refers to solid matrix material comprising a polymer which is covalently bonded to a functionalized indicator. The polymeric material of the sensor composition is permeable to oxygen, and is permeable or transparent to the wavelengths of light utilized in sensing the analyte of interest. Typically, the sensor composition is in the form of a film.

The "analyte of interest" is a substance which is found in the blood or body tissues of a patient. The concentration of the analyte of interest is determined on the basis of the measured concentration of the quencher [Q], i.e., a substance which quenches the signal emitted by the indicator, and the known relationship between the analyte and quencher.

The analyte of interest is either $O_2$ or a biomolecule, known hereinafter as an "oxygen-related analyte". Oxygen is a substance which quenches the fluorescence signal directly. Consequently, oxygen may act as the analyte of interest, the quencher, or both. An oxygen-related analyte is a substance that quenches the fluorescence signal indirectly through a known relationship with oxygen. The concentration of the oxygen-related analyte in the medium can be related to the concentration of oxygen that is present in the composition. For example, the Moreno-Bondi et al. article *Oxygen Optrode for Use in Fiber-Optic Glucose Biosensor*, *Analytical Chemistry*, Vol. 62, No. 21 (Nov. 1, 1990) describes a glucose sensor based on glucose dependent consumption of oxygen catalyzed by the enzyme glucose oxidase. The glucose oxidase is immobilized onto the surface of an oxygen sensing element. As the concentration of glucose in the external medium increases, more oxygen is consumed within the sensor composition, resulting in a change in the dynamic quenching of the fluorescence by oxygen. Glucose concentration is therefore computed as a function of the quencher concentration actually measured by the instrument. It is also well known in the art that enzymatic reactions involving adenosine triphosphate (ATP) or cholesterol result in the production or consumption of oxygen, and thereby enable oxygen optrodes to serve as transducers for these analytes.

As used herein the term "sensing element" refers to a sensor composition and a substrate for holding the sensor composition and for bringing it into contact with the medium which is to be analyzed. In one preferred embodiment the substrate is an optical fiber which has a film of the sensor composition disposed thereon. In another preferred embodiment, the substrate is a flow-through cassette which holds a sensor disk that, preferably, comprises the sensor composition and a clear plastic web support.

The functionalized indicator comprises a linker arm and a polyaromatic chelate metal complex comprising a luminescent platinum group metal and three ligands, at least one of which is a bidentate diphenylphenanthroline. If desired, the basic polynuclear aromatic compound may be derivatized with one or more other groups, i.e., non-functional substitutent groups such as alkyl groups, provided such derivatization does not substantially interfere with the emitted signal provided by the excited state complex. Such complexes by themselves are not suitable to be covalently bonded to the matrix material. Accordingly, such complexes are chemically modified to include at least one linker arm with a functional portion capable of chemically reacting with the matrix material or a precursor of the matrix material to covalently bond the functionalized indicator thereto. In a particularly useful embodiment, the complex is a ruthenium or osmium tris[diphenylphenanthroline] complex chemically modified to include one or more functionalized linker arms having a reactive group capable of reacting with and bonding to a silicone-based polymer and/or precursors thereof, such as polymethylhydrosiloxanes. The linker arms are attached to the phenyl moiety of a diphenylphenanthroline ligand. Preferably, the reactive group is a terminal reactive group. Suitable reactive groups for covalently bonding the functionalized indicator to a silicone based polymer or the precursors thereof include a hydroxy, an alkoxy, a halo, a carboxy, an acetoxy, a phenol, a siloxane, and a vinyl group. Such groups are capable of being hydrosilylated, for example, with a polymethylhydrosiloxane to covalently bond the indicator to the silicone-based polymer precursor. The resulting precursor or compound can be reacted with vinyl-terminated polysiloxanes, thereby forming an addition-cure silicone which is covalently bonded to the indicator. To provide a substantially homogenous distribution of the indicator throughout the sensing element, it is desirable that the functionalized indicator remain solubilized in the mixture of polymer precursors during curing.

Particularly, useful functionalized linker arms comprise alkenyl groups, substituted alkenyl groups, hydroxyalkyl groups, and the like. The linker arm preferably is comprised principally of an aliphatic group, although it may include one or more heteroatoms, such as an oxygen atom, a nitrogen atom, a sulfur atom, a silicon atom, one or more heterocyclic groups, one or more aryl groups, or a combination of heteroatoms and heterocyclic and/or aryl groups so long as the solubility of the functionalized indicator in a mixture of polymer precursors is maintained. The linker arm should have substantially no undue detrimental effect on the analyte sensitivity of emitted signal provided by the excited state complex.

Figure 1B:
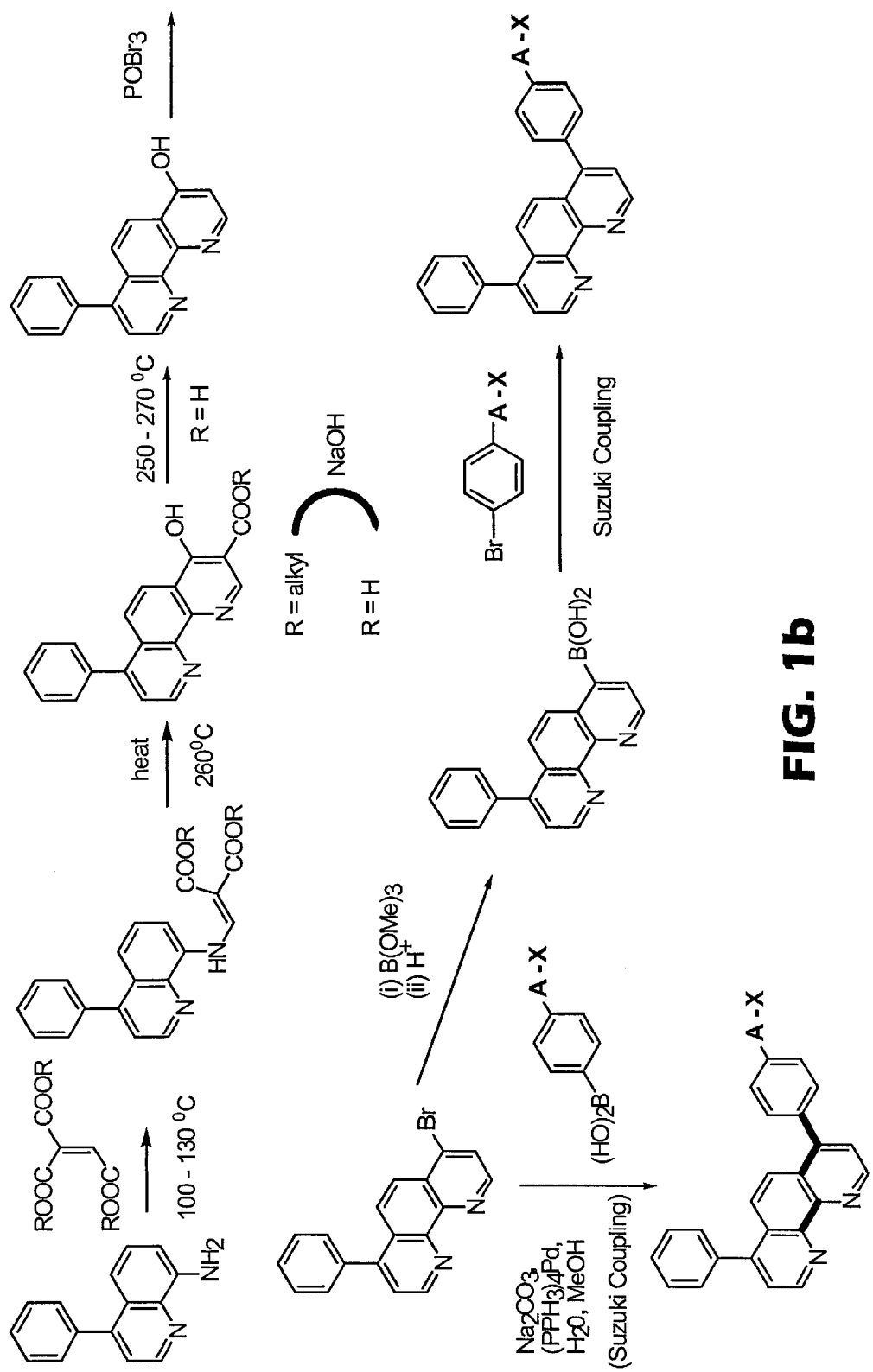
FIG. 1b is a synthetic scheme for making a functionalized ligand according to the present invention.

Various chemical modification techniques, many of which are conventional and well known in the art may be employed to prepare the functionalized indicator. Care should be taken to avoid destroying or even substantially diminishing the analyte sensitivity and intensity of the emitted signal in the process of functionalizing the complex. It has been found that sufficient sensitivity is maintained if the characteristic structure of the complex remains substantially unaffected, i.e., intact after the chemical modification. Schematics for two particularly suitable methods for preparing a functionalized indicator are shown in FIGS. 1a and 1b.

The amount of the indicator incorporated into the sensing element may vary over a broad range and depends for example, on the solubility of the functionalized indicator in the host matrix and concentration dependent self quenching of the fluorescent emission of the complex at higher concentration, i.e., mM.

In a particularly useful embodiment, the functionalized indicator has the formula:

$$M^+L_1L_2L_3,$$

wherein $M^+$ is $Ru^{2+}$, $Os^{2+}$; $Ir^{3+}$, or $Rh^{3+}$; ligands $L_1$ and $L_2$ are identical or different and represent an optionally substituted bidentate phenanthroline or diphenylphenanthroline ligand or an optionally substituted cyclometallated bidentate phenylpyridine or a benzo[h]quinoline ligand; and ligand $L_3$ is a bidentate diphenylphenanthroline ligand substituted by one or more linker arms which covalently bonds the complex to the matrix material. The linker arm, covalently bonded to the matrix material, comprises a group selected from the group consisting of a covalent bond, O, C(O)O, an optionally substituted methylene group, an optionally substituted carbon chain comprising 2–20 carbon atoms, and combinations thereof, wherein the carbon chain optionally comprises one or more of the following moieties or combinations thereof: an oxygen atom, a nitrogen atom, a sulfur atom, a silicon atom, a heterocyclic groups, and an aryl group. Representative functionalized indicators covalently bonded to the matrix material include, but are not limited to the following structures:

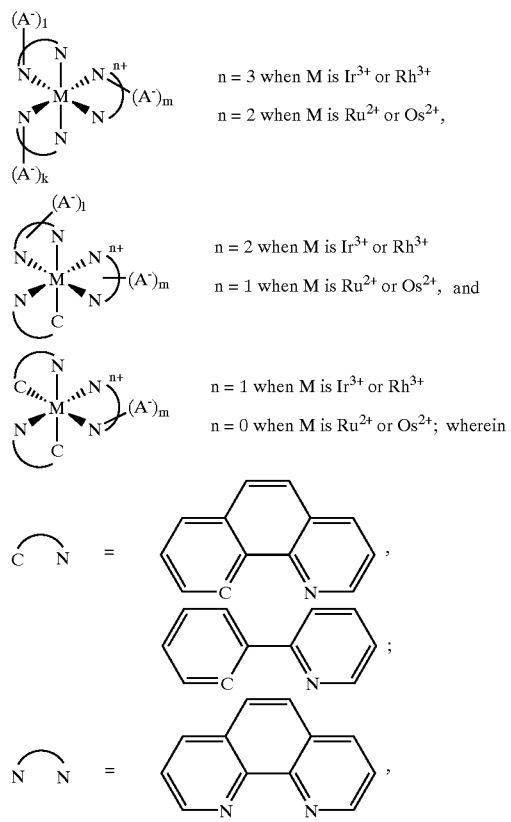

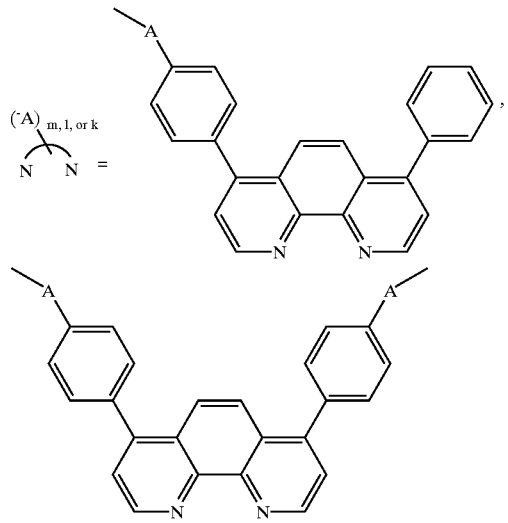

when m, l, or k = 1 or 2,

M is an iridium ($Ir^{3+}$), rhodium ($Rh^{3+}$), ruthenium ($Ru^{2+}$), or osmium ($Os^{2+}$) cation; A is a linker arm as described above, m is 1 or 2, and k and l are independently 0, 1, or 2. Prior to covalently bonding to the matrix material, the linker arm is in the form of a functionalized linker arm A—X, where X is a reactive group described above. The table below demonstrates the relationship between some preferred A—X (functionalized linking arms) and A (linking arms).

| —AX | —A— |
|---|---|
| —(CH$_2$)$_6$OH | —CH$_2$(CH$_2$)$_5$O— |
| —CH=CH$_2$ | —CH$_2$CH$_2$— |
| —CH$_2$CH=CH$_2$ | —CH$_2$CH$_2$CH$_2$— |

The ligands may have other substituents, as well, which do not significantly detract from compatibility of the functionalized indicator with the polymer matrix or polymer matrix precursor, nor unduly decrease the fluorescence lifetime of the functionalized indicator. Representative counter anions in the functionalized indicators (not shown above) may include but are not limited to organosulfonates, including 3-(trimethylsilyl)-1-propylsulfonate (DSS$^-$), organophosphates, tetraphenylborate, BF$_4^-$, Cl$^-$, Br$^-$, PF$_6^-$, SbF$_6^-$, ClO$_4^-$, and the like. Useful counter anions are compatible with the polymer matrix precursor and are not reactive with silyl hydrides. DSS$^-$, PF$_6^-$, and Cl$^-$ are preferred counter anions.

A number of synthetic routes to making the functionalized indicators may be envisioned by one skilled in the art. However, a preferred method may be illustrated in the preparation of bis(4,7-diphenyl-1,10-phenanthroline)(4-phenyl-7-para-hexanolphenyl-1,10-phenanthroline)ruthenium(II). In this method, dichlorotetrakis (dimethylsulfoxide)ruthenium(II) is reacted with 4,7-diphenyl-1,10-phenanthroline and lithium chloride. The resulting dichlorobis(4,7-diphenyl-1,10-phenanthroline)ruthenium(II) is then reacted with 7-para-hexanolphenyl-4-phenyl-1,10-phenanthroline and silver nitrate, producing bis(4,7-diphenyl-1,10-phenanthroline)(4-phenyl-7-para-hexanolphenyl-1,10-phenanthroline)ruthenium(II).

Any suitable polymeric material may be employed in the present sensing element provided that the polymeric material has no substantial detrimental effect on the function of the sensor system or on the medium being monitored. Because of their substantial gas and light permeability and aqueous impermeability properties, silicone-based polymeric materials are preferred. More preferably, cross-linked silicone-based polymeric materials are employed. For use in the bedside market, the polymeric material is preferably a cross-linked polydimethyl siloxane or a copolymer of dimethyl siloxane and diphenylsiloxane.

The precursor of the polymeric material, the polymer precursor, may be selected from one or more monomers, pre-polymers, and mixtures thereof. In one embodiment, the polymer precursor is a precursor of a vinyl/hydride addition cure polysiloxane polymer. A particularly useful polymer precursor when oxygen is the analyte of interest, is a vinyl terminated dimethyl siloxane. If the polymeric material is to be cross-linked, a cross-linking agent is included with the polymer precursor. Such cross-linking agents are preferably compounds which include at least three functional groups per molecule capable of reacting with the polymer precursor and/or a partially polymerized intermediate to form cross links, e.g., between polymer chains, in the polymeric material. A particularly useful cross-linking agent is methylhydrosiloxane/dimethylsiloxane copolymer, especially when the polymer precursor includes vinyl terminated dimethylsiloxane.

Figure 1C:
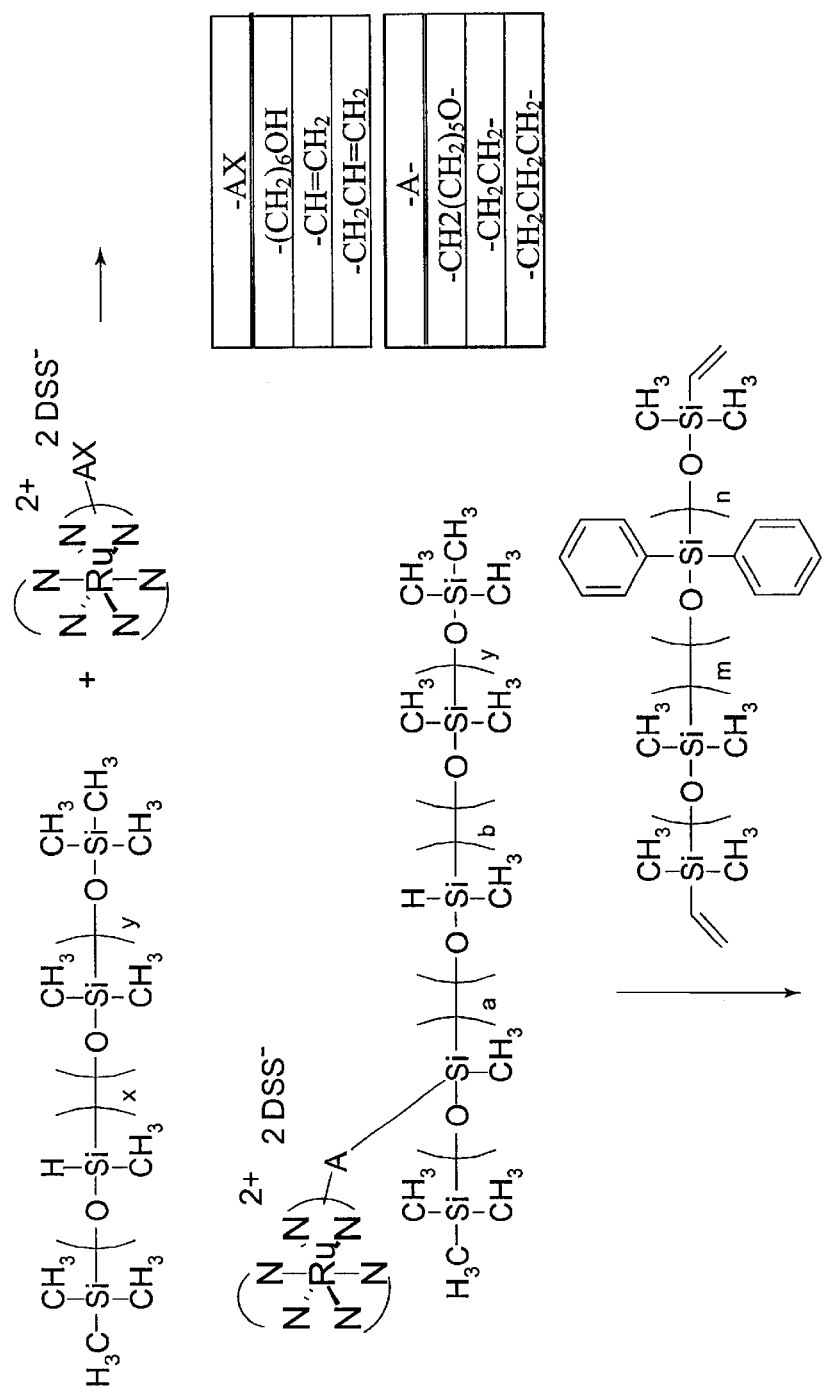
FIG. 1c is a reaction scheme for bonding the functionalized indicator to and forming a silicone based polymer matrix according to the present invention.

Of this group, polymers in which a major portion of the R groups (shown in the polyalkyl(aryl)hydrosiloxane formula above) are methyl are preferred because of the high gas permeability of such polymers. A sufficient number of hydride groups should be present to provide a satisfactory cross-linked or cured polymer, and preferably to covalently bond the indicator to the matrix material. It is of course realized that other members of the homologous series which include the above-noted polymers may also be used. The final silicone-based matrix material is cross-linked. Suitable vinyl terminated polysiloxanes include two or more functional vinyl groups which react with the hydride or hydro groups of the polyalkyl(aryl)hydrosilanes, for example, polymethylhydrosiloxanes, to form the cross-linked matrix material. Such cross-linking advantageously occurs in the presence of a catalyst, such as a platinum-containing catalyst. The properties of the cross-linked silicone can be varied by changing the degree of cross-linking, for example, by adjusting the concentration of the Si—H groups or component on the polyalkyl(aryl)hydrosiloxanes, for example, polymethylhydrosiloxanes, and/or the molecular weight of the vinyl-terminated polysiloxanes. A schematic for bonding the functionalized indicator to and forming a silicone-based polymer matrix according to the present invention is shown in FIG. 1c.

One or more catalysts may be used to promote the formation, by polymerization, of the polymeric material. One such catalyst is a divinyl platinum complex. The sensor composition precursor, including a catalyst component, may be exposed or subjected to elevated temperature sufficient to facilitate the catalyst component in promoting polymerization. Such elevated temperatures are greater than ambient temperature (22° C.) and preferably are in the range of about 40° C. to about 100° C. or more. The amount of catalyst component used should be sufficient to promote the desired degree of polymerization. The catalyst component should have no substantial detrimental effect on the functioning of the present system or on the medium being monitored. As used herein, the terms "polymerization" and "polymerizing" relate to one or more chemical reactions, including cross-linking, by which a polymer or polymeric material is formed.

In a useful embodiment, the catalyst component is chosen so as to be activated (for example, to promote polymerization of the polymer precursor), such as photo activated, upon being exposed to one or more factors, such as to light energy, preferably selected from visible light energy and ultraviolet light energy, and/or elevated temperatures, as defined herein, and the like. One substantial advantage of such a "factor" activated catalyst is that the polymer precursor, including the catalyst, can be prepared and maintained as such for relatively long periods of time by avoiding exposing the precursor to the "activating factor". Thus, one important process variable, that is the time when the polymer precursor is polymerized, in producing the present sensors is controlled so that the need to follow a tight production schedule because of the spontaneous polymerization of the polymer precursor is advantageously reduced. When it is desired to polymerize the polymer precursor, the precursor is simply exposed to the "activating factor". A particularly useful class of "factor activated" catalysts are those which are activated by light energy and, after being activated by sufficient light energy, are effective to partially polymerize the polymer precursor and are also effective upon being exposed to elevated temperatures to promote further polymerization of the partially polymerized polymer precursor.

Any suitable "factor" activated catalyst may be employed in the present invention, provided such catalyst has no substantial detrimental effect on the present system or on the medium being monitored. Photo-activated hydrosilylation catalyst systems are particularly useful. Certain platinum group metal-containing materials are very effective "factor activated" catalysts for use in the present invention. A number of such catalyst components are disclosed in Drahnak U.S. Pat. Nos. 4,510,094 and 4,530,879 and 4,600,484, and in Boardman et al U.S. Pat. No. 4,916,169, each of which is incorporated in its entirety herein by reference. Specific examples include cyclopentadienyl trimethyl platinum, derivatives thereof and mixtures thereof, particularly those which, after being activated by visible light energy or ultraviolet light energy, provide additional effective catalytic activity at elevated temperatures. The use of a combination of light energy and elevated temperatures to facilitate polymerization of the polymer precursor allows the polymerization to occur more rapidly and/or more completely relative to systems in which only light energy is employed.

In certain embodiments, the matrix material is formed from a diphenyl-dimethyl polysiloxane copolymer. Vinyl terminated diphenyl dimethyl polysiloxane copolymers having mole % diphenylsiloxane ranging from 3.0% to 23.5% are available commercially. Such polymers can be blended with the functionalized indicator, a cross-linking agent, and a catalyst to create a web coatable composition that can be cured photochemcially by photactivation of the catalyst. Alternatively, the functionalized indicator and cross-linking agent are first reacted and then blended with the base polymer and catalyst to create a composite that, subsequently, can be cured by activation of the catalyst. A particularly suitable cross-linking agent for this purpose is a trimethylsilyl terminated methylhydrosiloxane/dimethylsiloxane copolymer, which is also commercially available.

Both the crosslink density and the ratio of phenyl to methyl groups affect oxygen permeability and oxygen solubility, and therefore $K_{SV}$. $K_{SV}$ is decreased by increasing phenyl content in the matrix or increasing cross-link density. Since the solubility and the diffusion rate of oxygen in the polymeric matrix can be manipulated by varying the amount of the polydiphenylsiloxane in the matrix, such copolymers are useful for preparing sensing elements with reduced oxygen sensitivity. Such sensing elements are well-suited for determining oxygen concentrations in a medium, such as blood, where oxygen partial pressures range from about 40 mm Hg to 180 mm Hg. The exact formulation of the matrix is determined empirically using standard techniques.

Yafusso U.S. Pat. No. 5,508,509, which is specifically incorporated in its entirety herein, teaches that addition cured silicones comprising selected polyaromatic hydrocarbon fluorophores can be coated uniformly onto a clear plastic web and then cured to give a uniform sheet of sensing material from which individual and uniform sensor disks can be punched out.

Sensor Systems

In addition to the sensing element, the present sensor systems comprise an excitation assembly positioned and adapted to provide an excitation signal to the sensing element, a detector assembly that is positioned and adapted to detect the analyte-dependent emission signal from the sensing element and to provide a corresponding electrical signal, and a processor assembly that processes the detected signal to provide an output signal. The excitation assembly comprises a light source, preferably selected from the group consisting of light emitting diodes, laser diodes, frequency doubled laser diodes, and solid state light sources. The processor, which is coupled to the detector includes memory for storing information for characterizing a calibration relationship between analyte concentration and an analyte concentration dependent parameter. The processor assembly processes the detected signals to derive the concentration dependent parameter, and provides output signals representative of analyte concentration as a function of the derived concentration dependent parameter and the stored information.

In a preferred embodiment, the sensor system is a phase modulation sensor and comprises an excitation assembly configured to provide an intensity modulated, preferably a sine wave modulated, excitation signal to the sensing element, and a detection assembly configured to detect a corresponding intensity modulated emission signal from the sensing element. The processor assembly of the phase modulation sensor is positioned and adapted to analyze the modulated emission signal in determining the concentration of the analyte in the medium.

In practice, phase-modulation detection can be implemented in a number of different modes, all of which generate a concentration dependent parameter that varies as a function of analyte concentration. These phase-modulation detection modes include:

1. Phase shift vs. analyte concentration at constant modulation frequency;
2. Demodulation ratio vs. analyte concentration at constant modulation frequency;
3. Modulation frequency vs. analyte concentration at constant phase shift;
4. Modulation frequency vs. analyte concentration at constant demodulation factor; and
5. multi-frequency phase and/or modulation vs. analyte concentration.

The five modes differ with respect to the parameter, i.e. phase shift, demodulation factor, etc., which are used to determine analyte concentration in the medium. While any of the five modes may be utilized in the present sensors, the first three, generally, are easier to implement and are, thus, preferred.

In the first mode, the processor assembly is adapted to determine the extent of the phase shift between the modulated excitation signal and the modulated emission signal. The extent of this phase shift is dependent on the concentration of the analyte in medium.

In the second mode, the processor assembly is adapted to determine the ratio of demodulation factors between the modulated excitation signal and the modulated emission signal. The size of this ratio is dependent on the concentration of the analyte in the medium.

In the third mode, as in the first mode, the processor assembly is adapted to determine the extent of the phase shift between the modulated excitation signal and the modulated emission signal. In the third mode, however, the intensity modulated excitation signal is then adjusted in frequency to maintain a fixed phase shift between the modulated excitation signal and the modulated emission signal. The excitation frequency necessary to maintain this fixed phase shift is dependent on the concentration of the analyte in the medium.

In the fourth mode, as in the second mode, the processor assembly is adapted to determine the ratio of demodulation factors between the modulated excitation signal and the modulated emission signal. Here, though, the intensity modulated excitation signal is adjusted in frequency to maintain that ratio at a fixed value. The excitation frequency necessary to maintain this fixed ratio between demodulation factors is dependent on the concentration of the analyte in the medium.

In the fifth mode, the excitation signal contains multiple discrete frequencies and the phase shift and/or demodulation factor at each of several frequencies is used to determine analyte concentration. Systems of this type require deconvolution of the emission signal, for example by Fourier analysis software. The frequency domain information derived by this multi-frequency processing approach is further processed to obtain values for fluorescence lifetimes or Stern-Volmer slopes, and these values are in turn translated into analyte concentration. A disadvantage of these multivariant sensor systems is the additional complexity required for the excitation system, detector and processor to serially or simultaneously operate at many frequencies for each analyte.

For each of the phase-modulation sensors described above, one preferred embodiment comprises a sensing element for which the solid polymeric matrix material is a polymer which is permeable to the analyte of interest and the indicator is a luminescent platinum group metal complex comprising at least one bidentate diphenylphenanthroline ligand having a linker arm that covalently attaches to the polymer backbone. The emission from the complex in this matrix is characterized by a bimolecular quenching rate constant $k_q$ for quenching by oxygen and by one or more fluorescence lifetimes $\tau_o$ above a lowest lifetime $\tau_{oL}=1$ $\mu$sec in the absence of oxygen such that the Stern-Volmer constant $K_{SV}$ is greater than 0.009 mm$^{-1}$ and substantially uniform over the range of oxygen partial pressures of 40–180 mmHg.

The detector assembly is optically coupled both to the sensing element and the excitation assembly. Optical coupling can be achieved, for example, by use of fiber optic cable connections, optical light guiding elements, optical routing blocks such as those taught in U.S. Pat. No. 6,009,339, lens arrays and the like. The detector assembly includes a photo-detector which converts these light signals to electrical signals. The photo-detector may be, for example, a photodiode, an avalanche photodiode, or a photomultiplier tube. Preferably, the detector assembly is configured to alternately sample the modulated excitation signal and the modulated emission signal with a single photo-detector.

Preferably the detector assembly further includes an attenuation and switch component. This component receives the intensity modulated electrical output signals from the photo-detector, as well as a direct electrical signal from the oscillator which modulates the light emitted from the excitation assembly. This electric oscillator signal may be additionally used as a reference signal and must be attenuated to a comparable voltage as the two electric signals received from the photo-detector. The switch component alternatively passes on each of the three electrical signals.

Figure 2:
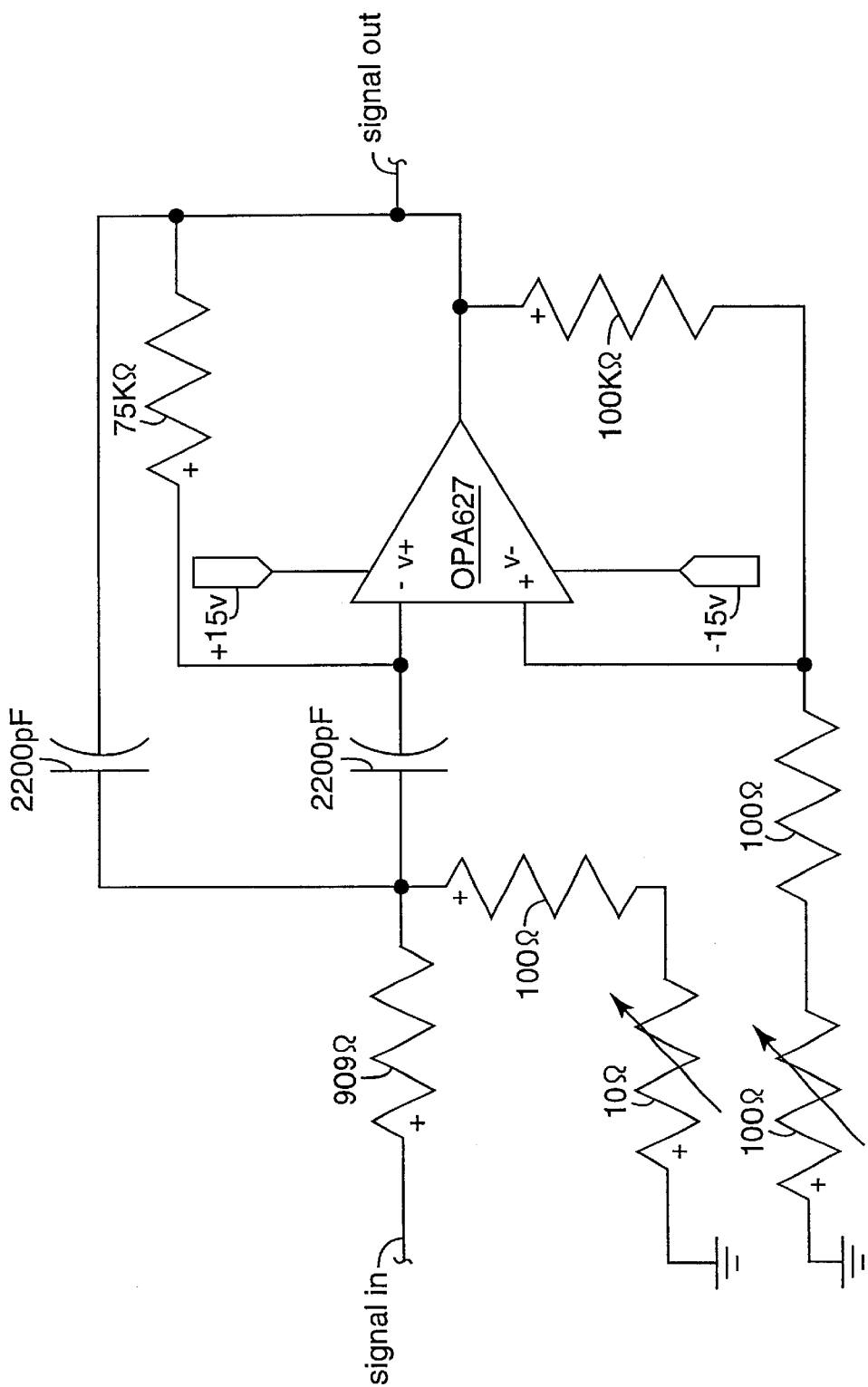
FIG. 2 is a schematic illustration of Delyiannis amplifier circuit used in one embodiment of a phase-modulation sensor system according to the present invention.
Figure 3:
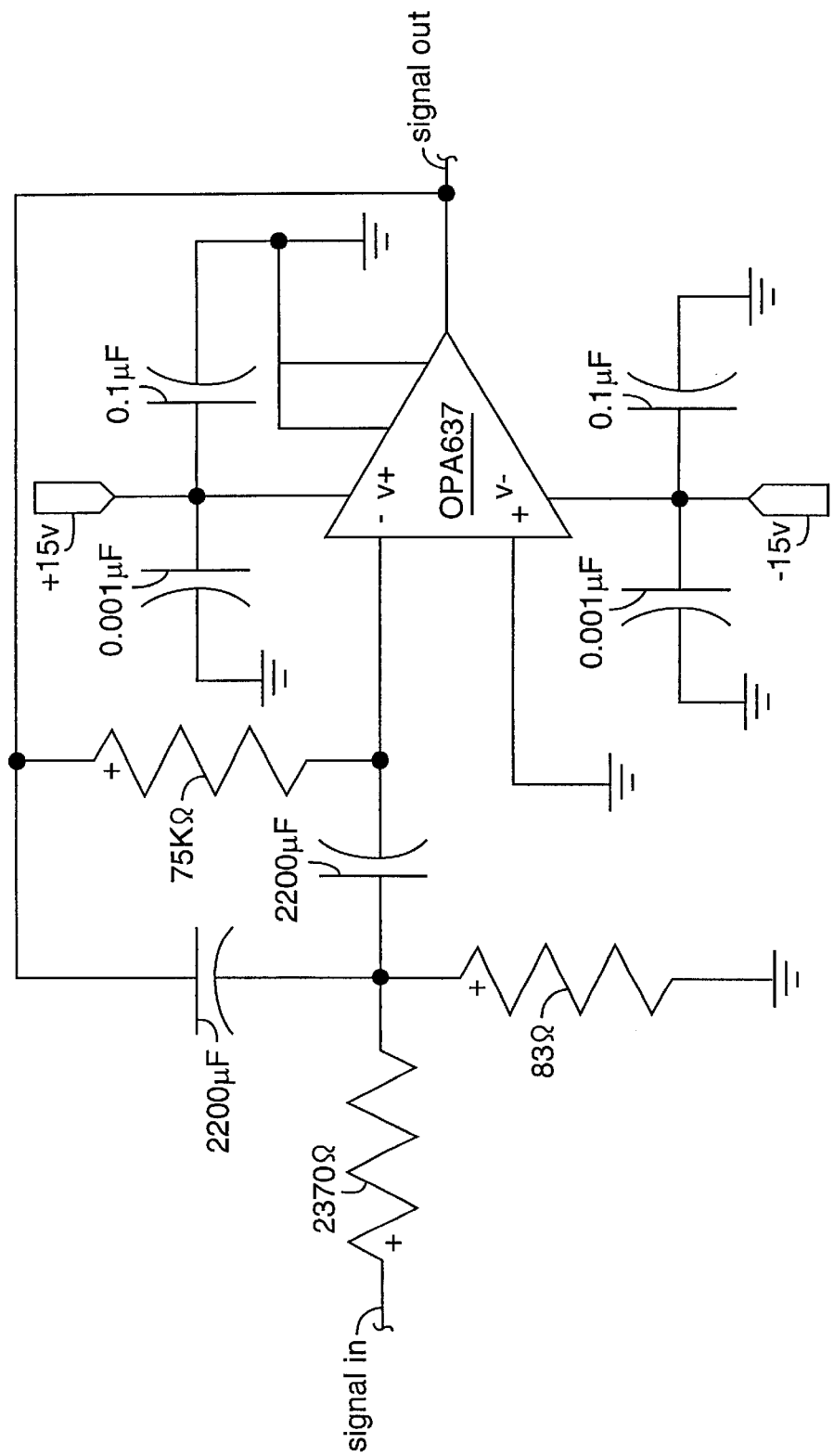
FIG. 3 is a schematic illustration of a multifeedback path amplifier circuit used in one embodiment of a phase-modulation sensor system according to the present invention.

Preferably, the detector assembly is also configured to electronically amplify and bandpass filter the intensity modulated electrical output signals from the photo-detector. Such amplification may be desirable, especially in an in-vivo application, because the amount of light received by the photo-detector is small, leading to a small electrical signal. Since photodiodes generally have small gain, it further may be desirable to use a photodiode and amplifier combination as the photo-detector. The gain added by an amplifier allows more stability for measuring variations in intensity and phase shift. The photodiode and amplifier can optionally be combined as an integrated device which can optionally be integrated with an analog to digital converter. In one preferred embodiment, the output of the photodiode is input to a high gain trans-impedance amplifier, also known as a pre-amplifier. The output of the pre-amplifier is optionally input to a bandpass filter/amplifier circuit to further improve the signal to noise ratio (SNR). Two suitable filter/amplifiers include a Delyiannis amplifier (FIG. 2) and a multi-feedback path (MFP) amplifier (FIG. 3). The component values shown in FIGS. 2 and 3 correspond to circuits built to amplify and filter signals with a modulation frequency of 30 kHz. The Delyiannis amplifier generally provides a higher gain and a better SNR than the MFP amplifier. However, the Delyannis amplifier generally requires more tuning than an MFP amplifier.

The bandpass filter receives electrical signals output from the pre-amp stage. The bandpass filter passes only those electrical signals within a frequency range centered around the modulation frequency of the excitation signal.

Preferably, electrical signals passing through the bandpass filter travel to an analog to digital converter ("A/D converter"). The A/D converter digitally samples the electrical signals and provides this signal to the processor assembly. Optionally, another A/D converter amplifies and digitally samples the intensity modulated electrical signal used to modulate the intensity of light emitted by the excitation assembly to provide these reference electrical signals to the processor assembly to correct for fluctuations in the excitation signal amplitude. If the excitation assembly emits a continuous light signal, leading to a continuous electrical signal, the A/D converter may sample only a part of the electrical signal multiple times. The results may be boxcar averaged to achieve accurate results. Alternatively, the excitation assembly may emit bursts of light, the results of which are boxcar averaged. A 200 msec burst of light every 6 seconds for 30 seconds provides enough data for an accurate measurement.

Optionally, the processor assembly is adapted to use the reference electrical signals traveling from the excitation assembly in more accurately determining the extent of the phase shift between the modulated excitation signal and the modulated emission signal. The processor assembly uses these reference electrical signals to determine the extent of the phase shift, relative intensity, relative demodulation factor, or other compared measurement between the modulated excitation signal and the modulated emission signal. Optionally, the processor assembly is adapted and configured to implement a digital least squares algorithm in determining the phase shift from the digitized modulated excitation signal and the digitized modulated emission signal.

The sensing element, excitation assembly, detection assembly, and processor assembly are configured to operate at one or more modulation frequencies not to exceed 1 MHz, preferably not to exceed 500 kHz, and more preferably, not to exceed 200 kHz. Preferably, the sensing system can operate sufficiently within the condition $[(k_q[O_2])^2+\omega^2]\tau_o^2 \gg 1+2k_q\tau_o[O_2]$ such that both slope of the relationship between the concentration dependent parameter and analyte concentration is independent of $\tau_o$ variability for all analyte concentrations within the operating range and for all lifetimes $\tau_o$ greater than $\tau_{oL}=1$ μsec. Preferably, the sensing element and the excitation signal are configured to provide an operating condition where the ratio $[(k_q[O_2])^2+\omega^2]\tau^2 \gg 1+2k_q\tau_o[O_2]$ exceeds 4, more preferably 6, and more preferably 10. Under these conditions, a constant calibration slope can be achieved and a rapid-single point calibration of the sensor is possible.

EXAMPLES

Example 1

Functionalized Ruthenium (II) Tris [Diphenylphenanthroline] Complexes

A. General Synthetic Approach

In a preferred embodiment, the indicator comprises a ruthenium (II) tris[diphenylphenanthroline] complex covalently attached to the polymer, which is preferably a cross-linked silicone. Thus, efforts were put forth to synthesize ruthenium sensor complexes with polymer attachable functionalities placed on one of the diphenylphenanthroline ligands. In this instance, previous literature reports (Evans, I. P.; Spencer, A.; Wilkinson, G. *Dalton Trans.*, 1973, 204–209. Cooley, L. F.; Larson, S. L.; Elliot, C. M.; Kelley, D. F. *J. Phys. Chem.*, 1991, 95, 10694–10700. Weaver, T. R.; Meyer, T. J.; et. al. *J. Amer. Chem. Soc.*, 1975, 97, 3039–3048.) had indicated the possibility of placing two like phenathroline ligands on Ru(II), followed by the addition of a third distinct phenanthroline based ligand in a subsequent step.

Efforts were pursued to synthesize functionalized diphenylphenanthrolines by a heterocyclic condensation route (FIG. 1a). Here, the ligand is constructed step-wise by a series of condensation reactions. This method is versatile in that one or two functionalized linker arms can be attached. For a mono-functionalized phenanthroline ligand, 2-nitroaniline is condensed with 3-chloro-1-phenylpropan-1-one to give 4-phenyl-8-nitroquinoline as reported by Case and Strohm (Case, F. H.; Strohm, P. F. *J. Org. Chem,* 1962, 27, 1641–1643) and expanded by Alford and coworkers (Alford, P. C.; Cook, M. J.; Lewis, A. P.; McAuliffe, G. S. G.; Skarda, V.; Thomson, A. J.; Glasper, J. L.; Robbins, D. J. *J. Chem. Soc.,* Perkin Trans. II, 1985, 705–709). In the following step, the nitro group is reduced to an amine using tin (II) chloride. The resulting 8-aminoquinoline can be again condensed with a substituted 3-chloro-1-phenylpropan-1-one to give the required mono-substituted 4,7-diphenylphenanthroline.

Alternatively, mono-functionalized phenanthroline ligands can be accessed as outlined in FIG. 1b. Here 4-bromo-7-phenylphenanthroline is obtained by reaction of 4-phenyl-8-aminoquinoline with an alkoxymethylenemalonic ester to give a 2-{[4-phenylquinolin-8-yl)amino]methylene}malonate intermediate. This intermediate can undergo ring closure condensation and ester hydrolysis to give the 4-hydroxy-7-phenyl-1,10-phenanthroline-3-carboxylic acid. Decarboxylation and bromination gives the 4-bromo-7-phenylphenanthroline synthon. The 4-bromo-7-phenylphenanthro line synthon is useful for performing coupling reactions with substituted phenylboronic acids using Suzuki coupling conditions. Alternatively 4-bromo-7-phenylphenanthroline can be converted to 7-phenyl-1,10-phenanthrolin-4-ylboronic acid and then reacted via Suzuki coupling with the corresponding substituted phenylbromides.

A preferred class of covalently attachable metal complexes of the present invention is prepared using substituted diphenylphenanthroline ligands comprising an alkenyl group, preferably a terminal alkenyl group (where the double bonded carbons bear three hydrogens). These novel ligands can be obtained via Suzuki coupling (Miyaura, N.; Suzuki, A., *Chem. Rev.*, 1995, 2457–2483) of the 4-bromo-7-phenylphenanthroline synthon with substituted phenylboronic acids of the general structure $(HO)_2B-C_6H_5-(CH_2)_nCH=CH_2$, where the alkenyl substituted phenyl boronic acids are prepared by the methods of Nakashima and Irie (Nakashima, H.; Irie, M., *Macromol. Chem. Phys.*, 200, 683–692). Alternatively, these ligands can be obtained via Suzuki coupling of the 7-phenyl-1,10-phenanthrolin-4-ylboronic acid with alkenylphenyl bromides of the general type $Br-C_6H_5-(CH_2)_nCH=CH_2$. Again, as in FIG. 1a, the corresponding novel vinyl-functional ruthenium complexes can be prepared by reaction of these ligands with dichlorobis(4,7-diphenyl-1,10-phenanthroline)ruthenium (II) in the presence of silver nitrate.

B. Synthesis of Specific Compounds

All chemicals were obtained from Aldrich Chemical Co. unless otherwise stated.

Synthesis of 8-Nitro-4-phenylquinoline

The procedure followed was similar to that of Case and Strohm (Case, F. H.; Strohm, P. F. *J. Org. Chem*, 1962, 27, 1641–1643). 2-Nitroaniline (3.83 g), arsenic acid (21.57 g), and an excess of phosphoric acid (30 mL) were heated to 100° C. 3-Chloro-1-phenylpropan-1-one (2.33 g) was added at such a rate as to ensure that the temperature did not exceed 120° C. The temperature was maintained between 120–130° C. for an hour, then raised to 140° C. for half an hour. The reaction mixture was cooled and poured onto ice. Potassium hydroxide (30% aqueous solution) was added to precipitate the product that appeared dark brown and tarry. The product was isolated on a glass filter, and was re-crystallized from hot toluene and petroleum ether.

Reduction of 8-Nitro-4-phenylquinoline to 8-Amino-4-phenylquinoline

The procedure followed was similar to that of Case and Strohm (Case, F. H.; Strohln, P. F., *J. Org. Chem*, 1962, 27, 1641–1643). 8-Nitro-4-phenylquinoline (5.0 g), tin chloride dihydrate (10 g Strem), and 50 mL of ethanol were combined and allowed to reflux for 8 hours. Basic water (100 mL) was added to precipitate the product. Filtration produced a tan solid material and an opaque filtrate. The solid material was dissolved and washed on the glass filter frit with ether. The filtrate was extracted with chloroform. Both the chloroform and ether solutions were combined and the solvent was removed to give a solid residue. $^1$H NMR analysis of this residue for separate runs showed the extent of reaction to be 90–100%.

Synthesis of tert-Butyl(dimethyl)[(6-phenylhexyl)oxy]silane

The procedure used was similar to that described by Corey and Venkateswarlu (Corey, E. J.; Venkateswarlu, A., *J. Am. Chem. Soc.*, 1972, 94, 6190–6191). 6-Phenyl-1-hexanol (14.0 g) and imidazole (13.36 g) were dissolved in dry DMF (40 mL). tert-Butyldimethylsilyl chloride (14.20 g,) was then added in one portion. The resulting solution was allowed to stir for 8 hours at room temperature. Aqueous sodium bicarbonate (100 mL, 10% by wt.) was then added and the resulting solution was allowed to stir for 15 minutes. The desired product was then extracted from the mixture with petroleum ether (3×250 mL). The petroleum ether extract was then washed with distilled $H_2O$ (7×300 mL), dried over $MgSO_4$ and roto-evaporated to give the desired product as a clear oil.

Synthesis of 1-[4-(6-{[tert-butyl(dimethyl)silyl]oxy}hexyl)phenyl]-3-chloropropan-1-one tert-Butyl(dimethyl)[(6-phenylhexyl)oxy]silane (21.00 g), 3-chlorophenylpropionyl chloride (9.14 g) and $CS_2$ solvent (100 mL) were placed in a two neck flask equipped with a reflux condenser. The mixture was then cooled to −78° C. and $AlCl_3$ (19.20 g) was added. The reaction mixture was stirred at −78° C. for 15 min., followed by: 0° C. for 20 min., 25° C. for 30 min., 40° C. for 40 min., 25° C. for 14 h. During the course of the temperature ramping, gas evolution (presumably HCl) was noted. The reaction was then quenched with several portions of 100 mL water/30 mL conc. HCl and the resulting mixture was transferred to a separatory funnel. The organic products were extracted into chloroform (4×200 mL). The chloroform fractions were combined and dried over $MgSO_4$. The solvent was then removed by roto-evaporation to give a tan oil which solidified on standing overnight. $^1$H NMR shows the presence of resonances consistent with the desired product.

Synthesis of 3-Chloro-1-[4-(6-hydroxyhexyl)phenyl]propan-1-one

1-[4-(6-{[tert-butyl(dimethyl)silyl]oxy}hexyl)phenyl]-3-chloropropan-1-one was purified on Analtech Tapered silica TLC plates, eluting with $CHCl_3$. A two dimensional pipette similar to that described by Rapoport (Klein, F. K.; Rapoport, H. *J. Chromatog.*, 1970, 47, 505–506) was used, where 100 mg of crude solid were dissolved in 10 mL $CHCl_3$, and two 0.5 mL spots were placed on each plate. Equipment was obtained to run 10 plates simultaneously. The desired band (low $R_f$) was scraped off of the plate using a razor blade and eluted with 10% methanol in chloroform. Forty percent of the original solid was isolated and found to be a 50:50 mol mixture of the desired 3-chloro-1-[4-(6-hydroxyhexyl)phenyl]propan-1-one and cyclic ether 4-oxabicyclo[10.2.2]hexadeca-1(14),12,15-trien-11-one. The material was used "as is" in the next synthetic step because the ether is inert towards the subsequent reaction pathway.

Synthesis of 6-[4-(7-phenyl-1,10-phenanthrolin-4-yl)phenyl]hexan-1-ol ($ph_2phenC_6H_{12}OH$)

The procedure followed was similar to that of Case and Strohm (Case, F. H.; Strohm, P. F. *J. Org. Chem*, 1962, 27, 1641–1643). 3-Chloro-1-[4-(6-hydroxyhexyl)phenyl]propan-1-one (0.73 g), 8-amino-4-phenylquinoline (0.27 g), arsenic acid (0.99 g) and 85% phosphoric acid (10 mL) were reacted as described in the procedure for the synthesis of 8-nitro-4-phenylquinoline. However during precipitation of the crude product, a pH of 6–8 was maintained in order to ensure that the alcohol functionality remained protonated. The crude product was re-crystallized with a 50:50 mixture of petroleum ether and chloroform. Further purification of the desired product was achieved using preparatory TLC with 2% methanol and 98% chloroform.

Synthesis of 4,7-dichloro-1,10-phenanthroline

In a flask was introduced 4,7-dihydroxy-1,10-phenthroline (5 g) and 50 mL $POCl_3$. This was refluxed for 6 hours. The cooled reaction mixture was slowly poured onto a mixture of crushed ice and ammonia solution with continuous stirring. Care was taken to keep the solution basic. This procedure generated a precipitate, which was filtered, washed with a mixture of water and p-dioxane (2×100 mL), and re-crystallization from ethanol-water to give 4,7-dichloro-1,10-phenanthroline as confirmed by $^1H/^{13}C$ NMR.

Synthesis of 4,7-bis(4-vinylphenyl)phenanthroline

A solution of 4,7-dichloro-1,10-phenantholine (0.28 g) in 20 mL toluene was mixed with 5 mL of water containing sodium carbonate (0.918 g) and $(Ph_3P)_4Pd(0)$ (0.043 g). The flask was sealed and thoroughly purged with nitrogen. To this was then added 4-vinylphenylboronic acid (0.36 g) followed by 2.5 mL ethanol. The purging procedure was repeated. The contents of the flask were refluxed for 4 days to give a precipitate on cooling. The precipitate was filtered, washed with petroleum ether and then air-dried. $^1H$ NMR spectroscopic evaluation was consistent with the desired compound.

Synthesis of 4-(4-bromophenyl)-8-nitroquinoline

2-Nitroaniline (3.73 g) and arsenic acid (7.10 g) were added to 25 mL of 85% phosphoric acid and the mixture heated under a nitrogen purge to 100° C., at which point 1-(4-bromophenyl)-3-chloropropan-1-one (10.21 g) was added. The reaction mixture was maintained at 120–130° C. for an hour and then at 140° C. for 15 min. After cooling to room temperature the reaction mixture was poured onto crushed ice and made alkaline with 30% KOH. Filtration gave a solid that was dissolved in toluene and dried over $MgSO_4$. Concentration gave two crops of product characterized by $^1H$-NMR as 4-(4-bromophenyl)-8-nitroquinoline.

Synthesis of 8-amino-4-(4-bromophenyl)quinoline

A solution of tin (II) chloride dihydrate (9.50 g) and 4-(4-bromophenyl)-8-nitroquinoline (4.60 g) in 50 mL absolute ethanol was refluxed for 6 hours. The reaction mixture was cooled to room temperature and then made alkaline with 30% KOH solution. The precipitated solid was filtered off, and dissolved in chloroform. The filtrate was extracted with ether. The ether extract and chloroform solution were combined and dried over $MgSO_4$. Evaporation gave a solid with $^1H$-NMR spectral signals consistent with 8-amino-4-(4-bromophenyl)quinoline.

Synthesis of 4,7-bis(4-bromophenyl)-1,10-phenanthroline

To a stirred solution of 8-amino-4-(4-bromophenyl)quinoline (2.0 g), arsenic acid (2.3 g) and orthophosphoric acid (6 mL) was added 1-(4-bromophenyl)-3-chloropropan-1-one (2.1 g). Care was taken during the addition that the temperature did not to exceed 120° C. The temperature was then ramped to 140° C. and kept there for 1.5 h. The reaction mixture was cooled to room temperature, poured onto ice and then made alkaline with 30% KOH. The precipitated solid was filtered off, washed with water and extracted with hot toluene. This solution was dried over $MgSO_4$ and evaporated to give 4,7-bis(4-bromophenyl)-1,10-phenanthroline as confirmed by $^1H$ NMR.

Synthesis of 4,7-bis(4-allylphenyl)-1,10-phenanthroline

In a Schlenk tube was dissolved a solution of 4,7-bis(4-bromophenyl)-1,10-phenanthroline (0.30 g) in 50 mL anhydrous tetrahydrofuran (THF). This solution was cooled in an acetone-dry ice bath followed by the addition of 1.30 mL of 1.0 M allyl(bromo)magnesium. The contents of the flask were allowed to stand for about 16 h while warming to room temperature. The solvent was then removed by roto-evaporation and the residue was taken up in chloroform. The chloroform solution was washed with water and dried over $MgSO_4$. Roto-evaporation to dryness gave a solid. $^1H$-NMR characterization suggested that the product was present together with unreacted 4,7-bis(4-bromophenyl)-1,10-phenanthroline.

Synthesis of Dichlorotetrakis(dimethyl sulphoxide) ruthenium(II); $RuCl_2(DMSO)_4$ The procedure used is based upon the work of Evans and coworkers (Evans, I. P.; Spencer, A.; Wilkinson, G., *Dalton Trans.*, 1973, 204–209). Ruthenium (III) chloride (10. g, Strem) was refluxed for 20 min. in 100 mL of degassed DMSO. The mixture was cooled to room temperature, combined with 50 mL of acetone and cooled to 0° C. to yield a yellow precipitate. This precipitate was filtered off, washed with acetone and ether, and dried. The product was re-crystallized from hot DMSO by addition of toluene and washing with petroleum ether. The desired product was confirmed by $^1H$-NMR, IR and elemental analysis.

Synthesis of dichlorobis(4,7-diphenyl-1,10-phenanthroline) ruthenium (II); $Ru(ph_2phen)_2Cl_2$ The procedure used is based upon the work of Cooley and coworkers (Cooley, L. F.; Larson, S. L.; Elliot, C. M.; Kelley, D. F. *J. Phys. Chem.*, 1991, 95, 10694–10700). $RuCl_2(DMSO)_4$ (3.0 g), 4,7-diphenyl-1,10-phenanthroline (=$ph_2phen$, 4.12 g, Lancaster), and lithium chloride (2.63 g, Fisher) were added to 560 mL DMF. The mixture was degassed using vacuum/nitrogen cycles and then heated at 125° C. for 30 minutes. The mixture was then cooled to room temperature, combined with 1 L of distilled water and extracted six times with 350 mL aliquots of chloroform. The organic layer was reduced in volume, dried over $Na_2CO_3$, filtered, and further reduced in volume to ca. 100 mL. 400 mL of ether was slowly added and the mixture was cooled to 0° C. overnight to yield a purple precipitate, which was isolated by filtration. Purification was achieved by column chromatography using silica gel (200–400 mesh, 60 Å) and 5% $CH_3OH$/95% $CHCl_3$.

Synthesis of Tris(4,7-diphenyl-1,10-phenanthroline) ruthenium(II) Chloride; $[Ru(ph_2phen)_3]Cl_2$ This compound was synthesized using the procedure given by Crosby (Crosby, G. A. et al., *J. Amer. Chem. Soc.*, 1971, 93, 3184).

Synthesis of Tris(4,7-diphenyl-1,10-phenanthroline) ruthenium(II) hexafluorophosphate; $[Ru(ph_2phen)_3](PF_6)_2$ The procedure for this reaction is based upon the work of Cooley and coworkers (Cooley, L. F.; Larson, S. L.; Elliot, C. M.; Kelley, D. F., *J. Phys. Chem.*, 1991, 95, 10694–10700). $Ru(ph_2phen)_2Cl_2$ (96.8 mg), $AgNO_3$ (39.5 mg, Merck), and 4,7-diphenyl-1,10-phenanthroline (38.4 mg, Lancaster) were dissolved in 60 mL of dry DMF (Aldrich Sure-Seal). The mixture was degassed under vacuum/nitrogen cycling and then heated to 110° C. for 40 minutes. The mixture was filtered after cooling to room temp. To the filtrate was added a solution of NaCl (15 mg) in 60 mL of distilled water. The mixture was again filtered. Three mL of 0.1 M $NH_4PF_6$ (aq) was then added and the mixture was cooled to 0° C., yielding a precipitate which was collected by filtration, dissolved in $CH_2Cl_2$, washed with distilled H$_2$O, and dried with anhydrous Na$_2$CO$_3$. Roto-evaporation gave a solid that was dried under vacuum to give the desired product as a solid.

Synthesis of Tris(4,7-diphenyl-1,10-phenanthroline) ruthenium(II) 3-(trimethylsilyl)-1-propane sulfonate; [Ru (ph$_2$phen)$_3$](DSS)$_2$ Ru(ph$_2$phen)$_3$Cl$_2$, (0.983 g) and 3-(trimethylsilyl)-1-propane sulfonate (DSS) (0.38 g), were dissolved in a mixture of 10 mL CH$_2$Cl$_2$ and 30 mL distilled H$_2$O. The light orange aqueous layer was decanted. An additional 0.354 g of DSS was added to the red-orange organic layer and the mixture was stirred. The organic layer was extracted with 3×30 mL portions of distilled H$_2$O. Additional CH$_2$Cl$_2$ was added with each transfer of the organic layer to minimize the loss of product during the transfers. The organic phase was dried over molecular sieves (4 Å), filtered, and reduced to dryness to yield the desired product Synthesis of Bis(4,7-diphenyl-1,10-phenanthroline)(4-phenyl-7-para-hexanolphenyl-1,10-phenanthroline) ruthenium(II) 3-(trimethylsilyl)-1-propane sulfonate; [Ru (ph$_2$phen)$_2$(ph$_2$phen-C$_6$H$_{12}$OH)] (DSS)$_2$ The procedure for this reaction is a modification of a procedure used by Cooley and coworkers (Cooley, L. F.; Larson, S. L.; Elliot, C. M.; Kelley, D. F. *J. Phys. Chem.*, 1991, 95, 10694–10700). A mixture of Ru(ph$_2$phen)$_2$Cl$_2$ (96.7 mg), 6-[4-(7-phenyl-1,10-phenanthrolin-4-yl)phenyl] hexan-1-ol (ph$_2$phenC$_6$H$_{12}$OH) (50.0 mg), AgNO$_3$ (40.2 mg, Merck), and dry DMF (60 mL, Aldrich Sure-Seal) was degassed using vacuum/nitrogen cycles and then heated under nitrogen to 130° C. for 30 minutes. Upon cooling, 60 mL of 5 mM NaCl was added to precipitate any remaining silver and to provide a chloride counter ion for the product. Metathesis to the 3-(trimethylsilyl)-1-propane sulfonate counter ion was achieved by first adding equal parts water and CH$_2$Cl$_2$ (180 mL each), followed by addition of sodium 3-(trimethylsilyl)-1-propane sulfonate (0.516 g). The desired product was extracted into the CH$_2$Cl$_2$ layer. The CH$_2$Cl$_2$ layer was then reduced in volume to near dryness using rotary evaporation to yield the desired product.

The following syntheses explanations are prophetic examples.

Synthesis of 4-{4-[6-(Allyloxy)hexyl]phenyl}-7-phenyl-1,10-phenanthroline

A 60% dispersion of NaH in mineral oil (76.1 mg) is suspended in DMF (10 ml). To this suspension is added 6-[4-(7-phenyl-1,10-phenanthrolin-4-yl)phenyl]hexan-1-ol (657 mg) followed by mixing at room temperature for 3 hrs. Allyl bromide (242 mg) is then added and the mixture is stirred at 35° C. for 24 hours, or until the reaction is judged complete by TLC. Excess NaH is carefully reacted with water and the reaction mixture is then diluted with ethyl acetate. The organic layer is washed with aqueous 6 M NaCl, dried over MgSO$_4$, concentrated by roto-evaporation, and purified by column chromatography on silica gel to give the desired product.

Synthesis of 4-p-methoxyphenyl-7-phenyl-1,10-phenanthroline 4-p-methoxyphenyl-7-phenyl-1,10-phenanthroline is made using the general procedures of Alford and coworkers (Alford, P. C.; Cook, M. J.; Lewis, A. P.; McAuliffe, G. S. G.; Skarda, V.; Thomson, A. J.; Clasper, J. L.; Robbins, D. J., *J. Chem. Soc.*, Perkin Trans. II, 1985, 705–709). To a stirring mixture of 8-amino-4-phenylquinoline (1.34 g), arsenic acid (2.3 g), and orthophosphoric acid (6 mL) is added p-methoxyphenyl-β-chloroethyl ketone (1.67 g) ensuring that the reaction temperature does not exceed 120° C. The temperature is then raised to 140° C. for 1.5 hours. The mixture is then cooled, poured onto ice, and made alkaline with 30% KOH, at which time a precipitate forms. The precipitate is collected by 30 filtration, washed with water, and extracted with boiling toluene. The resulting toluene solution is diluted further with methylene chloride and the mixture is dried over MgSO$_4$ then roto-evaporated to dryness to give the desired compound.

Synthesis of 4-p-hydroxyphenyl-7-phenyl-1,10-phenanthroline

Under a nitrogen atmosphere, an ice-cold solution of 4-p-biphenyl-7-p-methoxyphenyl-1,10-phenanthroline (2.72 g) in 1,2-dichlorobenzene is treated with BBr$_3$ (4.32 g). Stirring is continued for about 12 hours, during which time the ice-bath melts to room temperature. The reaction mixture is diluted with methylene chloride, washed with water and dried over MgSO$_4$ then roto-evaporated to dryness to give the desired product.

Synthesis of 4-[4-(pent-5-enyloxy)phenyl]-7-phenyl-1,10-phenanthroline 4-p-hydroxyphenyl-7-phenyl-1,10-phenanthroline (0.348 g) is reacted with Na metal (0.023 g) in ethylene glycol dimethyl ether (100 mL). To this mixture is added a solution of 5-bromo-1-pentene (0.20 g) in ethylene glycol dimethyl ether (10 mL). The resulting mixture is stirred at 35° C. for 24 hours, or until the reaction is judged complete by TLC. The reaction mixture is diluted with toluene, washed with 10% NaOH, washed with water and dried over MgSO$_4$. Roto-evaporation of the solvent gives a residue that is purified by column chromatography on silica gel.

Synthesis of 4-[4-(allyloxy)phenyl]-7-phenyl-1,10-phenanthroline 4-p-hydroxyphenyl-7-phenyl-1,10-phenanthroline (0.348 g) is reacted with Na metal (0.023 g) in ethylene glycol dimethyl ether (100 mL). To this mixture is added a solution of allylbromide (0.125 g) in ethylene glycol dimethyl ether (10 mL). The resulting mixture is stirred at 35° C. for 24 hours, or until the reaction is judged complete by TLC. The reaction mixture is diluted with toluene, washed with 10% NaOH, washed with water and dried over MgSO$_4$. Roto-evaporation of the solvent gives a residue that is purified by column chromatography on silica gel.

Synthesis of ethyl 4-hydroxy-7-phenyl-1,10-phenanthroline-3-carboxylate

Ethyl 4-hydroxy-7-phenyl-1,10-phenanthroline-3-carboxylate is made following general methods for synthesizing 3-alkoxycarbonyl-4-hydroxyquinolines as described by Price and Roberts (C. C. Price and R. M. Roberts, *J. Am. Chem. Soc.*, 1946, 68, 1204–1208). 8-amino-4-phenylquinoline (22 g) is mixed with diethyl ethoxymethylenemalonate (24 g). This mixture is heated at 130° C. until no more bubbles of ethanol could be detected coming from the mixture (ca 1 hr). The resulting mixture, which contains diethyl 2-{[(4-phenylquinolin-8-yl)amino] methylene}malonate intermediate is cooled to room temperature, added to hot diphenyl ether and heated to reflux for 45 minutes, to yield precipitation of the ring closed condensation product. The resulting mixture is cooled to room temperature to give a semi-solid mass, which is suspended in petroleum ether, washed twice with diethyl ether, and filtered to isolate the desired product.

Synthesis of 4-Hydroxy-7-phenyl-1,10-phenanthroline-3-carboxylic acid

Ethyl 4-hydroxy-7-phenyl-1,10-phenanthroline-3-carboxylate (5.37 g) is boiled with 10% aqueous NaOH (32 mL) for 2 hours, acidified with 10% HCl to yield a precipitate that is collected, washed with water and dried to give the desired product.

Synthesis of 4-bromo-7-phenyl-1,10-phenanthroline

4-Hydroxy-7-phenyl-1,10-phenanthroline-3-carboxylic acid is de-carboxylated in three gram amounts by heating at 250–270° C. in a Woods metal bath until effervescence ceases. A cake, principally comprising 7-phenyl-1,10-phenanthrolin-4-ol, cracks away from the sides of the beaker and is ground up in a mortar. This material is treated with excess phosphoryl bromide (15 mL) and the mixture is heated to 140° C. for 8 hrs. The reaction mixture is cooled to room temperature, and the remaining phosphoryl bromide is distilled off under reduced pressure to yield a semi-crystalline mass. This solid is stirred into a mixture of toluene and dilute sodium bicarbonate sufficient to make the mixture slightly basic. The mixture is stirred for several hours, after which time the toluene layer is separated and the aqueous layer is extracted with additional toluene. The toluene fractions are combined, treated with decolorizing charcoal, filtered, and evaporated to yield the desired product, which is collected by filtration and re-crystallized from toluene.

Synthesis of 7-phenyl-1,10-phenanthrolin-4-ylboronic acid

4-Bromo-7-phenyl-1,10-phenanthroline (1.42 g) is dissolved in THF solvent (15 mL). The mixture is cooled to −39° C. and added over a period of 20 minutes to an n-hexane solution of n-BuLi (1.5 M; 3.12 mL) which has been cooled to −78° C. The reaction mixture is stirred for 30 minutes, followed by the addition of trimethyl borate (0.49 mL) in THF at −39° C. is added over a period of 20 minutes. The reaction mixture is maintained at −78° C. for one hour, then allowed to warm to room temperature over a day. The reaction mixture is acidified with cold 2N HCl extracted with ether. The organic layer is extracted with 1 N NaOH and filtered. To the filtrate is added 2 N HCl at 0° C. to yield a precipitate, which is filtered, washed, dried and re-crystallized from ethanol to give the desired product.

Synthesis of 4-(4-but-3-enylphenyl)-7-phenyl-1,10-phenanthroline (Route A)

4-(4-Bromophenyl)-1-butene is made by the method of Peterson and coworkers (Peterson, P. E.; Chevli, D. M.; Sipp, K. A., *J. Org. Chem.* 1968, 33, 972). 4-(4-bromophenyl)-1-butene (0.42 g) and a solution of Pd(PPh$_3$)$_4$ (58 mg)) in 5 mL of degassed toluene are placed in a 50 mL Schlenk tube. The mixture is purged with nitrogen, after which a solution of 7-Phenyl-1,10-phenanthrolin-4-ylboronic acid (0.75 g) and Na$_2$CO$_3$ (0.428 g, 4 mmol) in 5 mL of degassed 4:1 H$_2$O/CH$_3$OH is added. The resulting mixture is heated tunder nitrogen at 100° C. with rapid stirring until TLC monitoring shows the reaction to be complete (ca 24 hrs). The reaction mixture is then added to a separatory funnel and extracted with ether (3×50 mL). The combined organic fractions are dried over MgSO$_4$ and concentrated by roto-evaporation. The desired product is purified by column chromatography on silica gel using a mixture of ethyl acetate and hexane.

Synthesis of 4-(4-{3-[diallyl(methyl)silyl]propyl}phenyl)-7-phenyl-1,10-phenanthroline 4-{3-[diallyl(methyl)silyl]propyl}phenylboronic acid is made by the method of Casado and Stobart (Casado, M. A.; Stobart, S. R., *Org. Lett.*, 2 (11), 2000, 1549–1552). 4-{3-[diallyl(methyl)silyl]propyl}phenylboronic acid (0.576 g) and a solution of Pd(Ph$_3$)$_4$ (58 mg) in 5 mL of degassed toluene is placed in a 50 mL Schlenk tube. The mixture is purged with nitrogen, after which a solution of 4-bromo-7-phenyl-1,10-phenanthroline (0.670 g) and Na$_2$CO$_3$ (428 mg, 4 mmol) in 5 mL of degassed 4:1 H$_2$O/CH$_3$OH is added. The mixture is heated under nitrogen at 100° C. with rapid stirring until TLC monitoring shows the reaction to be complete (ca 24 hrs). The reaction mixture is then added to a separatory funnel and washed with ether (3×50 mL). The combined organic fractions are dried over MgSO$_4$ and concentrated by roto-evaporation. The desired product is purified by column chromatography on silica gel using a mixture of ethyl acetate and hexane.

Synthesis of 4-(4-but-3-enylphenyl)-7-phenyl-1,10-phenanthroline (Route B)

4-(3-Butenyl)phenylboronic acid is made by the method of Nakashima and Irie (Nakashima, H.; Irie, M. *Macromol. Chem. Phys.* 200, 683–692). 4-(3-butenyl)phenylboronic acid (0.44 g) and a solution of Pd(Ph$_3$)$_4$ (58 mg) in 5 mL of degassed toluene is placed in a 50 mL Schlenk tube. The mixture is purged with nitrogen, after which a solution of 4-bromo-7-phenyl-1,10-phenanthroline (0.670 g) and Na$_2$CO$_3$ (428 mg, 4 mmol) in 5 mL of degassed 4:1H$_2$O/CH$_3$OH is added. The mixture is heated under nitrogen at 100° C. with rapid stirring until TLC monitoring shows the reaction to be complete (ca 24 hrs). The reaction mixture is then added to a separatory funnel and washed with ether (3×50 mL). The combined organic fractions are dried over MgSO$_4$ and concentrated by roto-evaporation. The desired product is purified by column chromatography on silica gel using a mixture of ethyl acetate and hexane.

Synthesis of Bis(4,7-diphenyl-1,10-phenanthroline)(4-phenyl-7-para-3-butenylphenyl-1,10-phenanthroline) ruthenium(II) 3-(trimethylsilyl)-1-propane sulfonate; [Ru(ph$_2$phen)$_2$(ph$_2$phen-but-3-enyl)](DSS)$_2$ The procedure for this reaction is a modification of a procedure used by Cooley and coworkers (Cooley, L. F.; Larson, S. L.; Elliot, C. M.; Kelley, D. F., *J. Phys. Chem.*, 1991, 95, 10694–10700). A mixture of Ru(ph$_2$phen)$_2$Cl$_2$ (96.7 mg), 4-(4-but-3-enylphenyl)-7-phenyl-1,10-phenanthroline (ph$_2$phen-but-3-enyl) (45.0 mg), AgNO$_3$ (40.2 mg, Merck), and dry DMF (60 mL, Aldrich Sure-Seal) is degassed using vacuum/nitrogen cycles and then heated under nitrogen to 130° C. for 30 minutes. Upon cooling, 60 mL of 5 mM NaCl is added to precipitate any remaining silver and to provide a chloride counter ion for the product. Metathesis to the 3-(trimethylsilyl)-1-propane sulfonate counter ion is achieved by first adding equal parts water and CH$_2$Cl$_2$ (180 mL each), followed by addition of sodium 3-(trimethylsilyl)-1-propane sulfonate (0.516 g). The desired product is extracted into the CH$_2$Cl$_2$ layer. The CH$_2$Cl$_2$ layer is then reduced in volume to near dryness using rotary evaporation to yield the desired product.

Synthesis of Bis(4,7-diphenyl-1,10-phenanthroline)(4-phenyl-7-para-diallylmethylsilylpropyl-1,10-phenanthroline)ruthenium(II) 3-(trimethylsilyl)-1-propane sulfonate; [Ru(ph$_2$phen)$_2$(ph$_2$phen-diallylmethylsilylpropyl)](DSS)$_2$ A mixture of Ru(ph$_2$phen)$_2$Cl$_2$ (96.7 mg), 4-(4-{3-[diallyl(methyl)silyl]propyl}phenyl)-7-phenyl-1,10-phenanthroline (=ph$_2$phen-diallylmethylsilylpropyl) (55.0 mg), AgNO$_3$ (40.2 mg, Merck), and dry DMF (60 mL, Aldrich Sure-Seal) is degassed using vacuum/nitrogen cycles and then heated under nitrogen to 130° C. for 30 minutes. Upon cooling, 60 mL of 5 mM NaCl is added to precipitate any remaining silver and to provide a chloride counter ion for the product. Metathesis to the 3-(trimethylsilyl)-1-propane sulfonate counter ion is achieved by first adding equal parts water and CH$_2$Cl$_2$ (180 mL each), followed by addition of sodium 3-(trimethylsilyl)-1-propane sulfonate (0.516 g). The desired product is extracted into the $CH_2Cl_2$ layer. The $CH_2Cl_2$ layer is then reduced in volume to near dryness using rotary evaporation to yield the desired product.

Synthesis of Bis(4,7-diphenyl-1,10-phenanthroline)(4-phenyl-7-para-allyloxyhexyl-1,10-phenanthroline) ruthenium(II) 3-(trimethylsilyl)-1-propane sulfonate; [Ru(ph$_2$phen)$_2$(ph$_2$phen-allyloxyhexyl)](DSS)$_2$ A mixture of Ru(ph$_2$phen)$_2$C12 (96.7 mg), 4-{4-[6-(allyloxy)hexyl]phenyl}-7phenyl-1,10-phenanthroline (ph$_2$phen-allyloxyhexyl) (53.0 mg), AgNO$_3$ (40.2 mg, Merck), and dry DMF (60 mL, Aldrich Sure-Seal) is degassed using vacuum/nitrogen cycles and then heated under nitrogen to 130° C. for 30 minutes. Upon cooling, 60 mL of 5 mM NaCl is added to precipitate any remaining silver and to provide a chloride counter ion for the product. Metathesis to the 3-(trimethylsilyl)-1-propane sulfonate counter ion is achieved by first adding equal parts water and $CH_2Cl_2$ (180 mL each), followed by addition of sodium 3-(trimethylsilyl)-1-propane sulfonate (0.516 g). The desired product is extracted into the $CH_2Cl_2$ layer. The $CH_2Cl_2$ layer is then reduced in volume to near dryness using rotary evaporation to yield the desired product.

Results

Spectral Characterization of [Ru(ph$_2$phen)$_3$](DSS)$_2$ and [Ru(ph$_2$phen)$_2$(Ph$_2$phenC$_6$H$_{12}$OH)](DSS)$_2$ Approximately $2\times10^{-5}$ M solutions of [Ru(ph$_2$phen)$_3$](DSS)$_2$ (1) and [Ru(ph$_2$phen)$_2$(ph$_2$phenC$_6$H$_{12}$OH)](DSS)$_2$ (2) were prepared in $CH_2Cl_2$. Both samples exhibited absorbance maxima at 442 and 464 nm and extinction coefficients of $3\times10^4$ $M^{-1}$ $cm^{-1}$ at 464 nm. The solutions were diluted by a factor of ten and purged with nitrogen to remove all oxygen. Fluorescence emission spectra were obtained for the nitrogen purged solutions using a SPEX Fluorolog 2™ Series spectrofluorimeter (SPEX Industries, Inc.; Edison, N.J.). Both samples were excited at 464 nm under identical conditions, giving rise to emissions centered at 608 nm. The relative emission intensities for each sample were normalized to the sample absorbances. Based on this analysis, it was determined that the relative fluorescence quantum efficiency of compound 2, $\phi_2$, is only slightly less than that of compound 1, $\phi_1$. The observed ratio was $\phi_2/\phi_1=0.81$. The fluorescence quantum yield of compound 1 is variously reported to be between 0.22 and 0.37, depending on solvent. Therefore, we estimate that the fluorescence quantum efficiency for compound 2 to be in the range of 0.18 to 0.3.

Sensitivity to Oxygen Quenching

Fluorescent emission from the dilute methylene chloride solutions of compounds 1 and 2 were measured under nitrogen and after equilibration with air (20.95% oxygen or 159.22 mmHg $O_2$). The emission for both compounds was quenched by air to a similar extent as shown in Table 1.

TABLE 1

Comparison of Stern-Volmer quenching rate constants for Compounds 1 and 2 in methylene chloride solution.

|  | $I_o/I_{air}$ | $K_{SV} = ak_q\tau_o$ (mm$^{-1}$) |
|---|---|---|
| Compound 1 | 11.0 | 0.0628 |
| Compound 2 | 10.6 | 0.0603 |

These results indicate that the incorporation of a pendant $C_6H_{12}OH$ group onto one of the phenyl rings of Ru(DPP)$_3^{2+}$ does not significantly change the efficiency of bimolecular quenching by oxygen.

Example 2

Sensor Films

A series of addition cure silicone sensor films containing covalently bonded [Ru(ph$_2$phen)$_3$](DSS)$_2$ moieties, derived from [Ru(ph$_2$phen)$_2$(ph$_2$phenC$_6$H$_{12}$OH)](DSS)$_2$ (2) were produced. The properties of the vinyl terminated polydimethylsiloxane polymers and the hydromethyl crosslinkers (available under the Petrarch trade name from United Chemical Technologies (UCT), Bristol, Pa.) used in these sensor films are given in Table 2, along with the corresponding UCT product numbers.

The formulations for a number of the sensor films are shown in Table 3.

TABLE 2

Properties of addition cured silicone materials used in making sensor films.

| Polydimethylsiloxane, Vinyldimethyl Terminated | | |
|---|---|---|
| | Viscosity | Wt % Vinyl |
| PS441 | 100 | 12 to 14 |
| PS442 | 500 | not reported |
| PS443 | 1000 | 0.18–0.26 |

| Methyl Hydro, Dimethylsiloxane Copolymer, Trimethylsilyl Terminated | | |
|---|---|---|
| | Viscosity | MW | Wt % Methyl Hydro |
| PS123 | 25–30 | 2000–2100 | 30–35% |

| Diphenyl Dimethyl Siloxane Copolymer, Vinyl Terminated | | | | |
|---|---|---|---|---|
| | mole % Dimethylsiloxane | mole % Diphenylsiloxane | MW | Viscosity |
| PS732 | 97 | 3 | 15,600 | 500 |
| PS782 | 84 | 16 | 9,300 | 500 |
| PS793 | 76.5 | 23.5 | 13,200 | 1500 |

TABLE 3

Formulations for sensor films made with addition cured siloxanes and $5 \times 10^{-4}$ M compound 2 [Ru(DDP)$_2$(DPPC$_6$H$_{12}$OH)](DSS)$_2$.

| Sensor | PS442 (parts per PS123 parts) | PS441 (parts per PS123 parts) | PS732 (parts per PS123 parts) | PS782 (parts per PS123 parts) | PS793 (parts per PS123 parts) | PS123 (parts) | % diphenyl | $I_o/I_{air}$ |
|---|---|---|---|---|---|---|---|---|
| A | 10 |    |    |    |    | 1 | 0    | 9.07 |
| B |    | 10 |    |    |    | 1 | 0    | 8.27 |
| C |    |    | 10 |    |    | 1 | 2.7  | 6.93 |
| D |    | 5  |    | 5  |    | 1 | 7.3  | 5.22 |
| E |    |    |    | 10 |    | 1 | 14.5 | 4.62 |
| F |    |    |    |    | 10 | 1 | 21.4 | 2.99 |

A. Sensor Films

The sensor films were prepared as follows. In a vial, 0.05 g of a polymethylhydrosiloxane (PS123 in Table 2) was mixed with 1 mL of CH$_2$Cl$_2$. In a separate vial, an amount (as indicated in Table 2) of a vinyl terminated dimethylsiloxane and/or diphenyl dimethyl siloxane was mixed with 0.5 mL of a $5 \times 10^{-4}$ M solution of [Ru(ph$_2$phen)$_2$(ph$_2$phenC$_6$H$_{12}$OH)](DSS)$_2$ (2) in CH$_2$CL$_2$, and 2 drops of a divinyl-platinum catalyst solution (available from UCT as product number PCO72, a platinum divinyl complex, 2–3% platinum concentration in xylene). This second mixture was allowed to cure for 5 minutes. Then the two vials were poured simultaneously into a flat-bottomed aluminum pan that was two inches in diameter. Thermal cure with evaporation of solvent gave rise to transparent thin films containing the covalently bound [Ru(ph$_2$phen)$_2$(ph$_2$phenC$_6$H$_{12}$O—)](DSS)$_2$ moiety.

A series of related sensor films having the same silicone materials as sensor films B and F were prepared by the same procedure as is outlined above, except the concentration of the [Ru(ph$_2$phen)$_2$(ph$_2$phenC$_6$OH)](DSS)$_2$ (2) solution was varied as follows: $1 \times 10^{-4}$ M, $5 \times 10^{-4}$ M, $1 \times 10^{-3}$ M, $5 \times 10^{-3}$ M.

The diphenyl/dimethyl ratios of sensor films C, D, E, and F, are 2.7%, 7.3%, 14.5% and 21.4%, respectively, as shown in Table 3.

Addition cured compositions of the types described above were also cast onto M-sol treated polyethylene, polycarbonate, or Zeonex films. The polymer films were treated by first soaking in 5% m-sol for 15 minutes, the allowing them to dry. The films were then laid flat. The addition cure silicone mixture was then coated onto the m-sol treated side of the film and covered with a glass jar to ensure slow evaporation of the solvent to prevent bubbles and precipitation.

After curing, sensor disks were then cut from the coated film construction and attached to a flow through cassette using Epoxy 5 minute glue and held tightly in place to make an even seal.

Sensor Films Prepared Using the Vinyl Terminated Ruthenium Complexes [Ru(ph$_2$phen)$_2$(ph$_2$phen-but-3-enyl)](DSS)$_2$, [Ru(ph$_2$phen)$_2$(ph$_2$phen-diallylmethylsilylpropyl)](DDS)$_2$, and [Ru(ph$_2$phen)$_2$(ph$_2$phen-allyloxyhexyl)](DSS)$_2$ In one preferred embodiment, sensor films were prepared using each of the following vinyl terminated ruthenium chelate complexes: [Ru(ph$_2$phen)$_2$(ph$_2$phen-but-3-enyl)](DSS)$_2$, [Ru(ph$_2$phen)$_2$(ph$_2$phen-diallylmethylsilylpropyl)](DSS)$_2$, [Ru(ph$_2$phen)$_2$(ph$_2$phen-allyloxyhexyl)](DSS)$_2$. In a vial, 0.05 g of a polymethylhydrosiloxane (PS123 in Table 2) is mixed with 1 mL of CH$_2$Cl$_2$. In a separate vial, 0.5 g of a vinyl terminated dimethylsiloxane (PS441 in Table 2) was mixed with 0.5 mL of a $5 \times 10^{-4}$ M solution of the ruthenium chelate complex in CH$_2$CL$_2$, and 2 drops of a divinyl-platinum catalyst solution (available from Huls America, Inc. as product number PCO72, a platinum divinyl complex, 2–3% platinum concentration in xylene). This second mixture is allowed to cure for 5 minutes. Then the two vials are poured simultaneously into a flat-bottomed aluminum pan that was two inches in diameter. Thermal cure with evaporation of solvent gives rise to transparent thin films containing the covalently bound [Ru(ph$_2$phen)$_2$(ph$_2$phen-A-)](DSS)$_2$ moiety.

Results

Sensor Film Fluorescence

Sensor films A–F were equilibrated with 1 atmosphere of nitrogen in the housing of a SPEXs fluorolog 2™ spectrophotometer operated in a front face emission geometry. Sensor films were excited at 464 nm and emission intensity, $I_o$, from covalently bound compound 2 was monitored at 608 nm. The sensor films were then equilibrated with 1 atmosphere of air (oxygen partial pressure of 159 mm Hg or 20.9%) and the emission intensity, $I_{air}$, was measured again. The presence of oxygen significantly reduced the emission intensity for each of the sensor films. The oxygen dependent fluorescence quenching was entirely reversible. Ratios of $I_o/I_{air}$ are given in Table 3.

Sensor films A and B, which have only dimethylsiloxane polymer and are quenched by oxygen to the greatest extent, exhibited quenching ratios of $I_o/I_{air}$=9.07 and 8.27 respectively. These numbers are less than the quenching ratio observed for compound 2 in methylene chloride ($I_o/I_{air}$= 10.6). This is believed to result from a lower solubility and permeability for oxygen in dimethylsilicone vs. methylene chloride. Sensor films C–F have increasing of diphenylsiloxane content in predominantly dimethylsiloxane films. As the diphenyl siloxane content increases, the quenching ratio decreases as shown in Table 3. Sensor film F had the highest diphenylsiloxane content of the sensor films we prepared (23.5% diphenylsiloxane), and exhibited the lowest quenching ratio $I_o/I_{air}$=2.99.

Leaching of Indicator

Sensor films A and F were each soaked in separate solutions of 0.5 mL of methylene chloride for 24 hrs in an effort to establish whether compound 2 was indeed covalently anchored into the siloxane film. Control sensor films G and H made with the non-covalently attachable compound 1 in the same polymers as sensor films A and F, respectively, were also tested. The absorption intensity for the ruthenium compound in each of the sensor films was measured at 464 nm on an absorption spectrophotometer before and after the 24 hr soak. In the case of sensor films A and F, the absorbance was unchanged to the limits of our detection (±0.3%), suggesting that compound 2 was indeed covalently attached to the siloxane matrix. For sensor films G and H, the absorbance at 464 nm dropped by 36% and 28% respectively, suggesting that unbound compound 1 was leaching from these films. The separate solutions of methylene chloride used to soak each film were purged with nitrogen and tested for residual ruthenium complex using the SPEX fluorometer under conditions where a $10^{-6}$ M solution of the ruthenium complex could be detected. The soak solutions associated with sensor films A and F showed no appreciable emission at 608 nm, while the soak solutions for sensor films G and H showed strong emission from dissolved compound 1. These results indicate that compound 1 leaches out of dimethylsiloxane sensor films, while compound 2 is covalently attached and does not leach out.

Preparation of Control Sensor Films

Control sensor films were prepared from [Ru(ph$_2$phen)$_3$]Cl$_2$ and [Ru(ph$_2$phen)$_3$](DSS)$_2$ complexes by blending them into dimethyl silicone films or soaking dimethylsilicone films in CH$_2$Cl$_2$ solutions of these complex. Each of these sensor films exhibited oxygen sensitive responses. However, we encountered difficulties in providing a reproducible sensor slope when these complexes were incorporated into dimethylsilicones or into dimethyl-diphenylsilicone copolymers. Also, we found that the complexes leached readily from the sensor films when exposed to a variety of organic solvents.

Example 3

30 kHz LED Phase Breadboard

Figure 4:
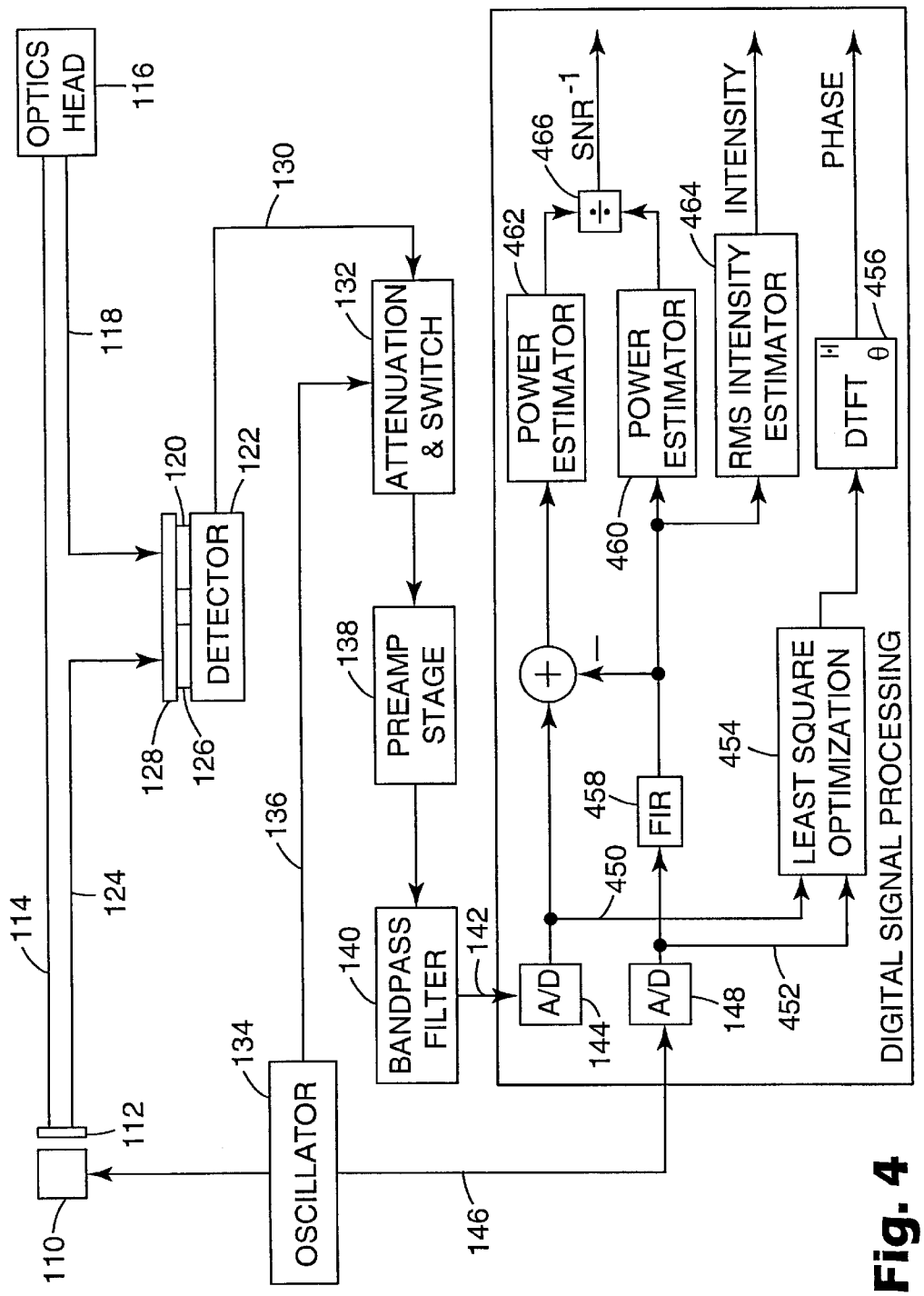
FIG. 4 is a schematic illustration of a 30 kHz phase breadboard using a least squares digital signal processing algorithm.

FIG. 4 shows a schematic illustration of the 30 KHz LED phase-modulation breadboard used to test amplitude and phase-modulation based oxygen sensing with the oxygen sensor systems of this invention.

GaN LEDs (from Nichia) 110 were amplitude modulated at a 30 kHz carrier frequency, a burst duration of 0.2 seconds, a repetition rate of 5 sec, and an average output power of 2.5 mW. The light was focused, passed through a band-pass excitation filter 112 (450 nm±25 nm; % T=52%; out of band blocking=0.001% T; available from Spectro-Film; Woburn, Mass.), and refocused into a multi-fiber optical excitation cable 114. At the distal end, the fibers of the excitation cable were randomly bifurcated with fibers from a multi-fiber optical emission cable. The distal end was terminated in an optical head 116 adapted to receive a flow through cassette. The optical emission cable returned modulated fluorescent return optical signal 118 to a band-pass emission filter 120 (610±35 nm; % T=64%; out-of-band blocking=0.001% T) such as is available from SpectroFilm. The filtered optical output was focused onto the active region of an H5783 photo-multiplier sensor module or an S1337-33-BR™ photodiode detector 122 (both available from Hamamatsu). A small fraction of the excitation fibers were directly routed 124 to the detector assembly and attenuated with a neutral density filter 126 to provide a reference optical signal from the LED.

Using a computer-controlled optical shutter 128, the photodetector alternately sampled the excitation/optical referencing signal 124 and the fluorescent return optical signal 118. This provided optical referencing to correct for fluctuations in the LED output amplitude. In addition, an electronic attenuation and switch 132 was used to alternately sample the detector photosignal 130 and a 30 KHz electrical reference signal 136 from the frequency generator 134. The detector output was directed to a three-stage electronic circuit that converted the photocurrent from the photodiode detector to a voltage. The attenuation and switch 132 was used to attenuate an electrical reference signal 136 from the LED drive oscillator and switch between this attenuated electrical reference signal 136 and an unattenuated photosignal 130. The transimpedance preamplification stage 138 converts the photosignal 130 or the electrical reference signal 136 to a voltage using an OPA627 operational amplifier circuit. The following stage was a two stage Delyiannis-style bandpass filter 140 using two OPA627 operational amplifiers. One of the two identical stages is illustrated in FIG. 2. This stage band-limits the noise power while further amplifying the signal. The gain of the three-stage circuitry was $7.3 \times 10^8$ V/A (177 dB) and was band-limited to 400 Hz with approximately 30 kHz center frequency. In a second reduction to practice, the output from the transimpedence preamplification stage 138 was input to a two stage MFP filter/amplifier, of which one of the two identical stages is illustrated in FIG. 3.

The amplified and filtered signal 142 from the bandpass filter 140 and a reference electrical signal 146 from the frequency generator 134 were digitally sampled 144 and 148 at 100 kHz and processed using LabVIEW™ virtual instrument software using a least squares estimation of the phase, intensity, and signal-to-noise ratio (SNR). Under these sampling conditions the noise power was further band limited to about 12.5 Hz, further increasing the SNR.

In operation, LabVIEW™ software alternately sampled the optical signal 118 from the sample, the optical referencing signal 124, and the electronic referencing signal 136. The optical referencing signal 124 corrected for LED fluctuations and the electronic reference signal 136 corrected for electronic drift associated with temperature, humidity and radio frequency (RF) rectification. Light level measurements indicated that, with optical coupling losses, a 20 nW fluorescent return harvested by the photodiode detector was sufficient to support high SNR's when combined with pulse integration methods. Using an OPA627 op-amp with a 10 kHz bandwidth (10 Mohm feedback and 1.4 pF capacitor) and a gain of 5 V/$\mu$W, the 20 nW fluorescent return provided a 100 mV electrical signal, at a noise floor of 100 $\mu$V per pulse. This gave a noise floor of 0.1% per pulse. Further improvements were made by averaging multiple pulses, giving an SNR of 50 dB. Stability tests performed continuously over a 50 hour period showed that referenced phase shifts remained stable to within 0.02 degrees and referenced amplitudes remained stable to within 0.1%.

Example 4

Digital Signal Processing

Novel digital signal processing algorithms were developed to determine the phase shift and demodulation ratio of the above-described sensor films. From these parameters, the oxygen dependent fluorescence lifetimes of the indicators in the sensor films can be determined.

Figure 5:
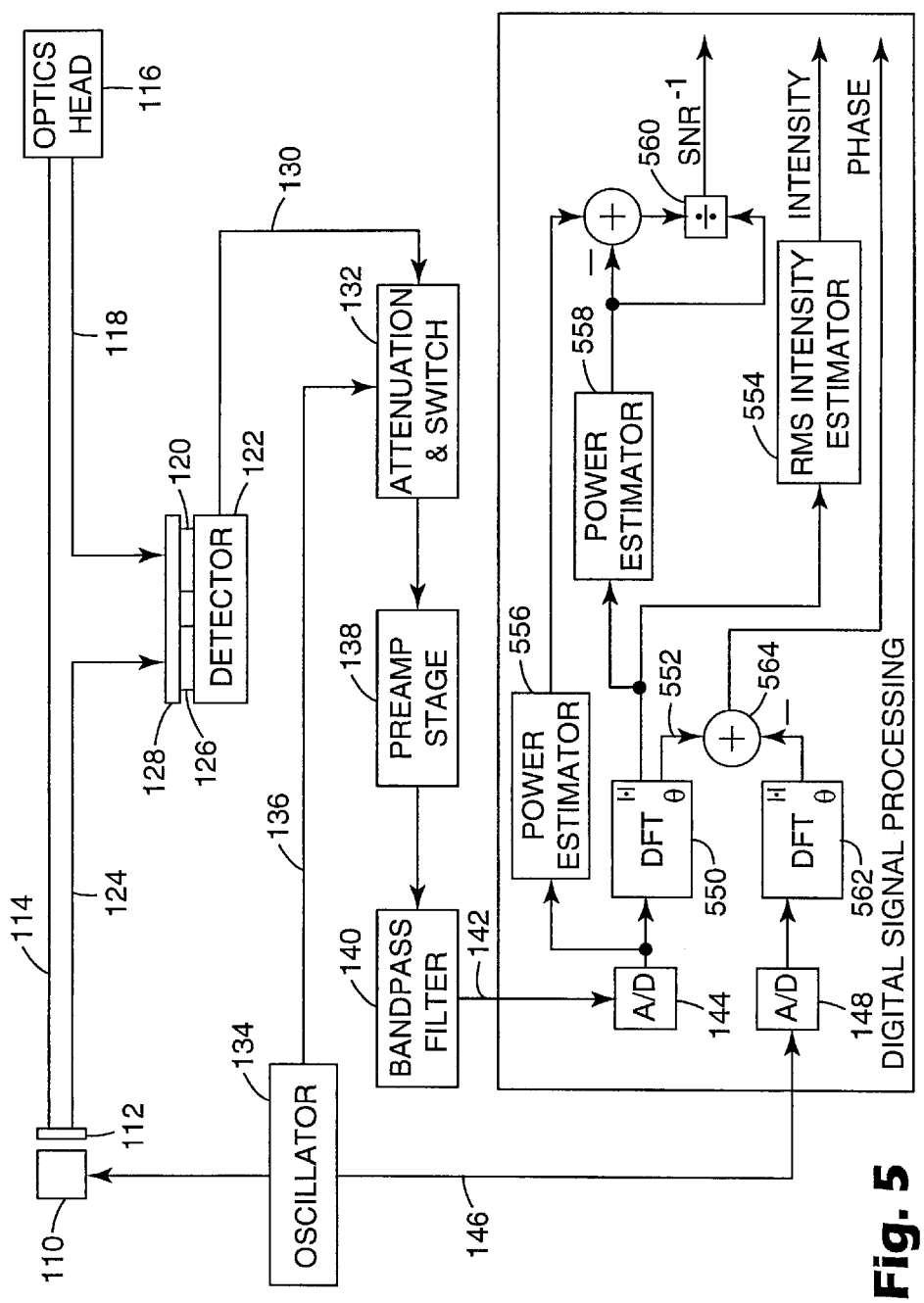
FIG. 5 is a schematic illustration of a 30 kHz phase breadboard using a fourier vector digital signal processing alogorithm.

Both a Fourier approach and a least-squares approach were implemented in LabVIEW software on a breadboard used at a modulation frequency of 30 kHz (Example 3). FIG. 4 shows schematically the opto-electronics and the digital signal processing associated with the least squares approach. For the Fourier approach, shown in FIG. 5, the opto-electronics portion of the breadboard remained the same. Only the Labview implementation of the algorithms changed.

For phase detection in the present implementation, the waveforms that must be digitized are the sensor signal $$x_s(t) = A_s \sin(2\pi f_m t + \phi_s) + g_s(t)$$
$$= p_s(t) + g_s(t)$$

and the reference signal $$x_r(t) = A_r \sin(2\pi f_m t + \phi_r) + g_r(t)$$
$$= p_r(t) + g_r(t)$$

where $g_s(t)$ and $g_r(t)$ are the noise terms and $f_m$ is the modulation frequency. For the 30 kHz breadboard, baseband detection necessitates $f_m$=100 kHz. The phase angles $\phi_s$ and $\phi_r$ represent cumulative phase shifts that the signals encounter through their respective opto-electronic signal paths. Only the difference between these phase angles is relevant to blood gas measurement. Sampling theory requires that the digitization rate be at least twice the bandwidth of the signal of interest. For the nominal modulation frequency of 30 kHz and a noise bandwidth of 1 kHz, a convenient digitization rate of 100 kHz was employed. This was a pre-set sampling frequency on the data acquisition boards. The sampled sensor and reference signals are, respectively, $$x_s(k) = A_s \sin(2\pi f_m k T_s + \phi_s) + g_s(kT_s)$$

and $$x_r(k) = A_r \sin(2\pi f_m k T_s + \phi_r) + g_r(kT_s)$$

where $$T_s = \frac{1}{f_s}$$

is the sampling period and $$f_s = \frac{1}{T_s}$$

is the sampling frequency.

The phase, intensity and signal-to-noise ratio (SNR) may be measured with a Fourier estimation. The normalized Discrete-Time Fourier Transform (DTFT) 550 of $x_s(k)$ at the modulation frequency is a complex number given by $$X_s(j\omega_m) = \frac{1}{N} \sum_{k=0}^{N-1} x_s(k) e^{-j\omega_m k}$$

where $$\omega_m = 2\pi \frac{f_m}{f_s}$$

is the normalized digital frequency in radians and N is the number of sample points acquired.

The phase 552 of $x_s(k)$ at the modulation frequency is given by $$\psi_s(j\omega_m) = \tan^{-1}\left(\frac{\text{Imag}(X_s(j\omega_m))}{\text{Real}(X_s(j\omega_m))}\right)$$

and the magnitude or intensity 554 is given by $$M_s(j\omega_m) = 2\sqrt{\text{Imag}(X_s(j\omega_m))^2 + \text{Real}(X_s(j\omega_m))^2}.$$

Note that the Fourier magnitude is not the RMS amplitude. In the absence of noise, the Fourier magnitude would be $A_s$ which is the true amplitude of the sensor signal. The true amplitude of a sinusoid is related to the RMS amplitude by $M = \sqrt{2} 2_{rms}$. As it is, the Fourier magnitude is a good estimate of the true amplitude or intensity since for large N the DTFT is a narrow bandpass filter.

With this in mind, a reasonable estimate of SNR is $$SNR_f = \frac{\frac{M_s^2(j\omega_m)}{2}}{\frac{1}{N}\sum_{k=0}^{N-1} x_s^2(k) - \frac{M_s^2(j\omega_m)}{2}}.$$

Here the numerator is the estimated power of the sinusoidal component $p_s(k)$ 558 and the denominator is the estimated power of the noise term $g_s(k)$. The noise power estimate is given by the total power of the sensor signal 556 minus the estimated power of the sinusoidal component $p_s(k)$ 558. It is assumed that $p_s(k)$ and $g_s(k)$ are uncorrelated.

By repeating the DTFT for the reference signal 562, the estimated phase difference 564 between the sensor and reference signals is given by $$\hat{\theta}_f = \psi_s(j\omega_m) - \psi_r(j\omega_m)$$

Both the Fourier phase and magnitude estimates can be made more accurate by synchronously sampling the sensor signal. Sampling in this fashion guarantees that an integral number of periods are collected and eliminates truncation error. For large N, however, the error is small.

As shown in FIG. 4, a least squares estimation 454 may be utilized instead of the Fourier estimation, and generally is preferred. The basic principle is to find a set of digital filter coefficients such that the squared difference between the sensor signal 450 and the filtered reference signal 452 is minimized. In other words, $$\min_h \sum_{n=0}^{N-1} \left( x_s(n) - \sum_{k=0}^{L-1} x_r(n-k) h(k) \right)^2$$

where [h(k)] is the set of L filter coefficients. The reference signal 452 is used since it is a high SNR signal with a frequency identical to the sensor signal 450. The filter coefficients simply scale and phase shift the clean reference signal so that it matches the sensor signal. Accordingly, the DTFT 456 of these filter coefficients at c m will yield the phase difference between the sensor and reference signals $$\hat{\theta}_{ls}(j\omega_m) = \tan^{-1}\left(\frac{\text{Imag}(H(j\omega_m))}{\text{Real}(H(j\omega_m))}\right).$$

One advantage of the least squares approach over the Fourier approach is that it is much less sensitive to errors in the modulation frequency $f_m$. The reason for this is that the sensitivity of the DTFT to frequency offsets will increase as the size of the DTFT increases. In the direct Fourier approach the size of the DTFT is N which is the number of sample points acquired. Typically, N is over 1000 while the size L of [h(k)] is normally 2 (only two filter coefficients are necessary to arbitrarily phase shift and scale a sinusoid.) In general, longer collect intervals (larger N) will reduce the variance of the phase estimate. However, in practice frequency errors may negate this advantage for Fourier estimation. The least squares approach is sensitive to the modulation frequency but it is not dependent on the number of sample points acquired. The least squares technique allows the collect interval to be increased with much less sensitivity to frequency mismatch.

The least squares approach assumes that the noise terms are uncorrelated with the signals and that the SNR of the reference signal is very high. Experimental results validate these assumptions.

The error residual of the least squares optimization, $$e(n) = x_s(n) - \sum_{k=0}^{L-1} x_r(n-k)h(k)$$
$$= \hat{g}_s(k)$$

is an estimate 462 of the noise term $g_s(k)$. The filtered reference signal 458, $$y(n) = \sum_{k=0}^{L-1} x_r(n-k)h(k)$$
$$= \hat{p}_s(k)$$

is an estimate 460 of the sinusoidal sensor component $p_s(k)$. As such, the RMS amplitude of the sensor signal can be estimated 464 as $$\tilde{M}_{ls} = \sqrt{\frac{1}{N}\sum_{k=0}^{N-1} y^2(k)}$$

and the SNR can be estimated 466 as $$SNR_{ls} = \frac{\frac{1}{N}\sum_{k=0}^{N-1} y^2(k)}{\frac{1}{N}\sum_{k=0}^{N-1} e^2(k)}.$$

The Fourier and least squares techniques are implemented in software. As such, they are easy to modify and upgrade, and both methods can be implemented in the same instrument with virtually no added cost. Moreover new estimation algorithms can easily be added via software revisions. The basic architecture (FIGS. 4 and 5) would remain the same. Although the Fourier and least squares methods have essentially the same performance in Gaussian noise, in other noise environments their performance may differ. Algorithms can be optimized for the particular noise present in the optoelectronic circuits.

The most significant factor in estimator performance is the collect interval: the longer the collect interval, the better the estimate. Increasing the sampling frequency in order to increase the number of samples in an interval will not improve performance in general. As long as the Nyquist criterion is satisfied, the sampling rate will not affect performance.

A desirable feature in many signal processing systems is synchronous sampling. This is not shown in FIG. 4 or 5, but the illustrated circuits could be modified at a moderate cost. Synchronous sampling links the A/D converter sampling rate to some other clock or oscillator in the system. In the case at hand, the A/D sampling rate would simply be synchronized to the reference signal. The A/D sampling rate would need to be quadrupled in order to satisfy the Nyquist sampling criterion. This sort of frequency multiplication is not difficult to implement. With a synchronous sampling system it will be possible to eliminate the A/D converter on the reference signal because its sampling phase would always be known. In addition, the estimation algorithms would be virtually immune to frequency errors and offsets. This is a significant advantage.

Figure 6:
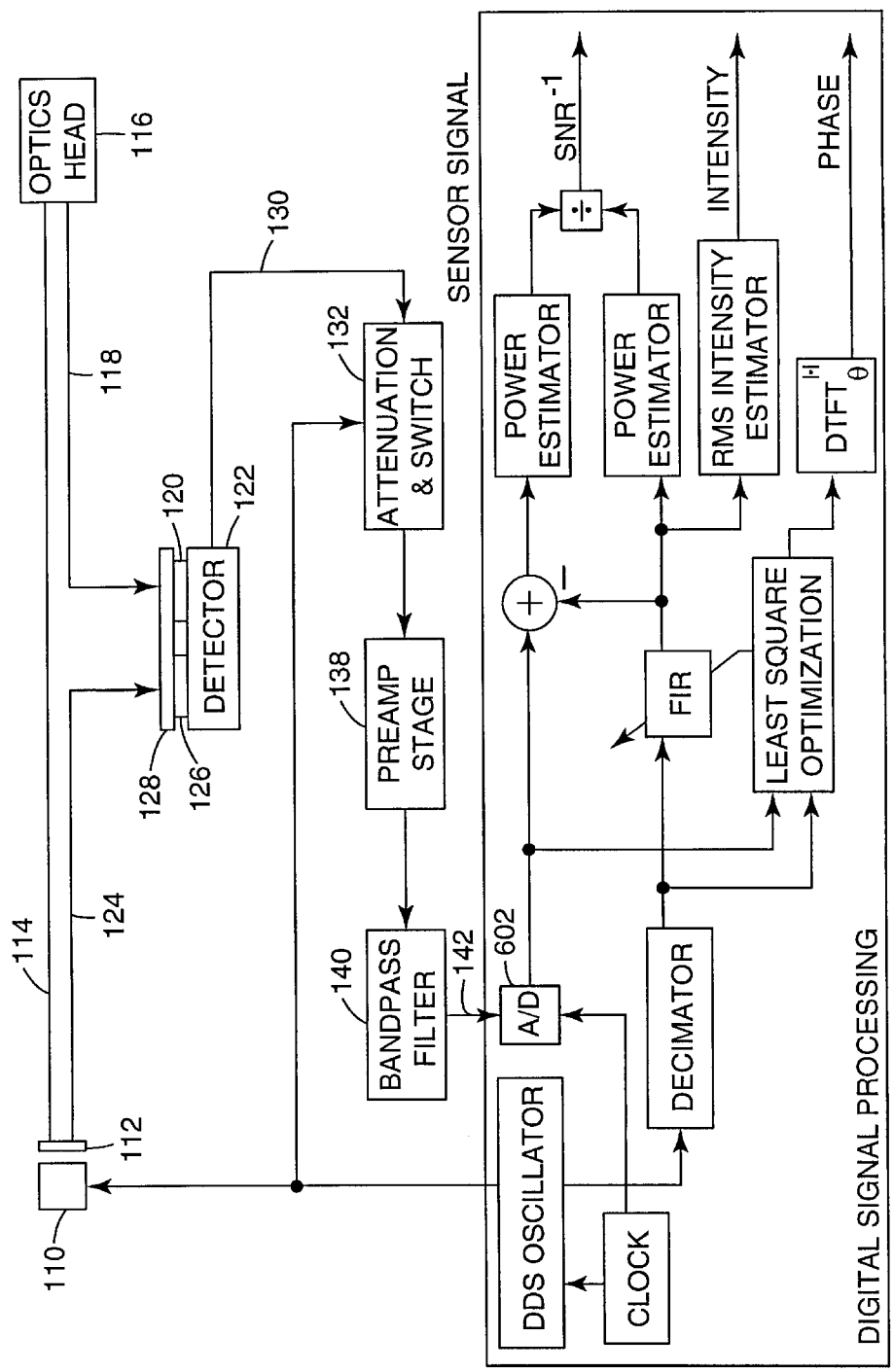
FIG. 6 is a schematic illustration of a 30 kHz breadboard using direct digital synthesis method of signal generation, using a least squares digital signal processing system.

Direct Digital Synthesis (DDS) is a signal generation technique that has become popular in instrumentation and telecommunication equipment. Essentially, it is a very fast digital-to-analog converter. DDS has many advantages. One is its ability to generate arbitrary waveforms. More important is its accuracy and precision as a sinusoidal waveform generator. The phase of a DDS signal can be very precisely controlled. FIG. 6 shows a DDS system which has been implementated on a breadboard. Note that only one A/D converter 602 is necessary in this implementation since the DDS phase is known. Digital phase estimation is a powerful alternative to analog techniques.

Example 5

Phase-modulation Fluorescence Detection of Oxygen Partial Pressures Using the 30 kHz Phase Breadboard and Sensor Films A and F.

Sensor film A was heat staked to the $O_2$ channel of a S400 flow through cassette (CDI/3M Health Care; Tustin, Calif.). Sensor film F was heat staked to the $O_2$ channel of a second S400 flow through cassette. These two sensor films were tested separately on the 30 kHz phase breadboard. First the sensor cassettes were connected to the S400 optics head of the breadboard. A thermostated 25 mM sodium phosphate buffer (pH 7.6, 37° C.) was then pumped through the sensor cassette in a closed loop system. The buffer reservoir was successively sparged with each of five precision gas mixtures comprising 0.00, 5.00, 10.0, 15.0, and 20.0% oxygen in nitrogen. The amplitude and phase shift of the fluorescent emission from the sensor cassettes were measured and stored on the computer.

Figure 7:
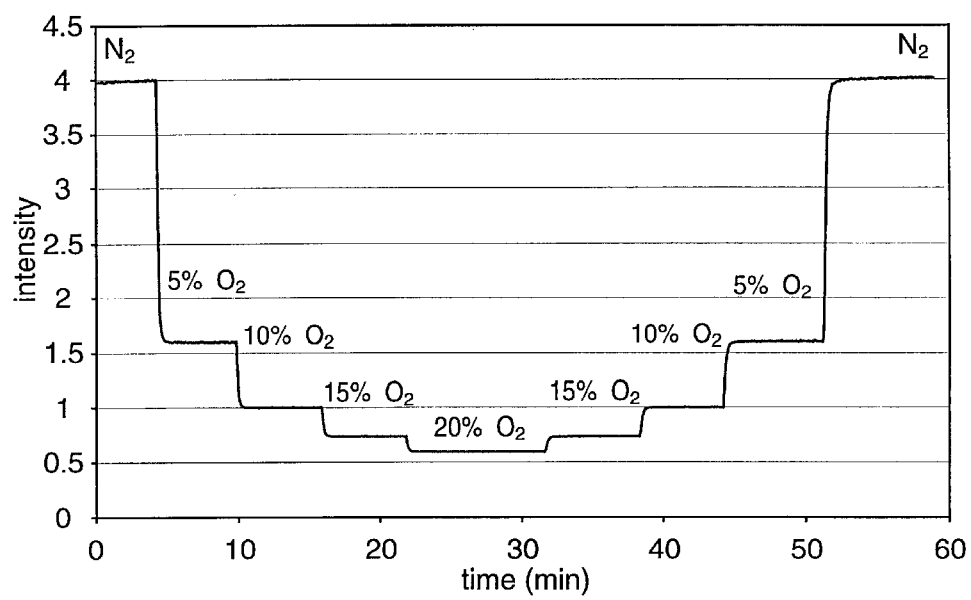
FIG. 7 is a graph showing fluorescence intensity as a function of oxygen partial pressure for sensor film A as measured on the 30 kHz phase breadboard.
Figure 8:
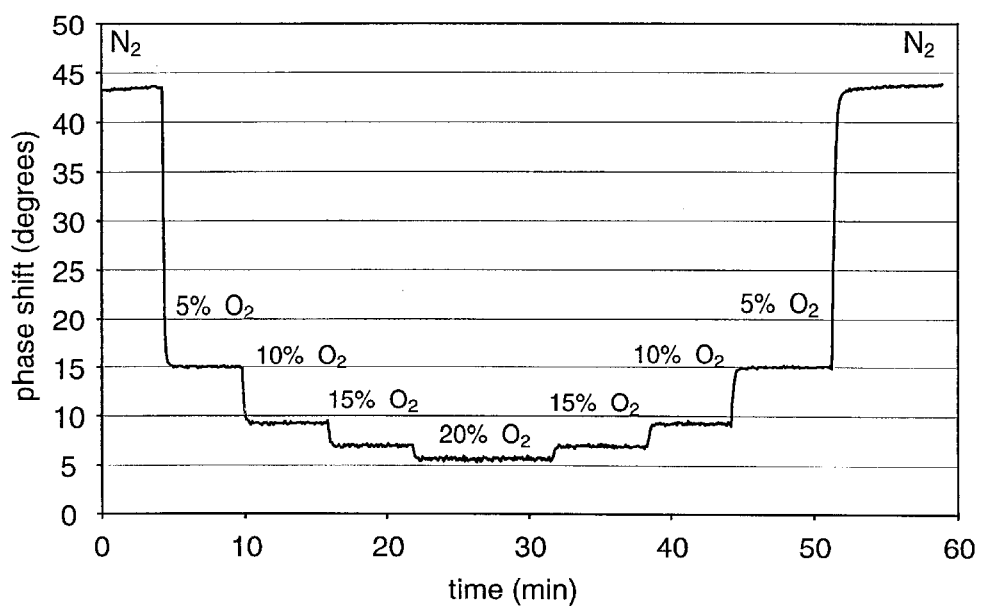
FIG. 8 is a graph showing phase shift as a function of oxygen partial pressure for sensor film A as measured on the 30 kHz Phase breadboard.

FIGS. 7 and 8 show the amplitude and phase shifts obtained for sensor film A as a function of oxygen partial pressure. Clearly, the amplitudes and phase shifts show a significant dependence on oxygen partial pressure for sensor film A. These plots show that sensor fluorescent response responds in a reversible and reproducible way with oxygen partial pressure. FIGS. 7 and 8 show that sensor film A (made with 100% dimethylsiloxane) exhibits the greatest oxygen sensitivity between 0 and 5% oxygen partial pressure. The fluorescence intensity drops by 59% and the phase shift drops by 65% (or 28.3 degrees) on going from 0% to 5% oxygen. For certain applications, such as trace oxygen detection in a bioreactor, this high sensitivity is preferred. Again referring to FIGS. 7 and 8, it can be seen that as the oxygen partial pressure increases stepwise from 5 to 10, to 15, and to 20%, that the changes in fluorescent intensity and in phase shift become less and less. For example, the change from 15% to 20% oxygen partial pressure produces an additional 3.8% decline in fluorescence intensity and an additional 2.7% decline (or 1.19 degrees) in phase shift.

Figure 9:
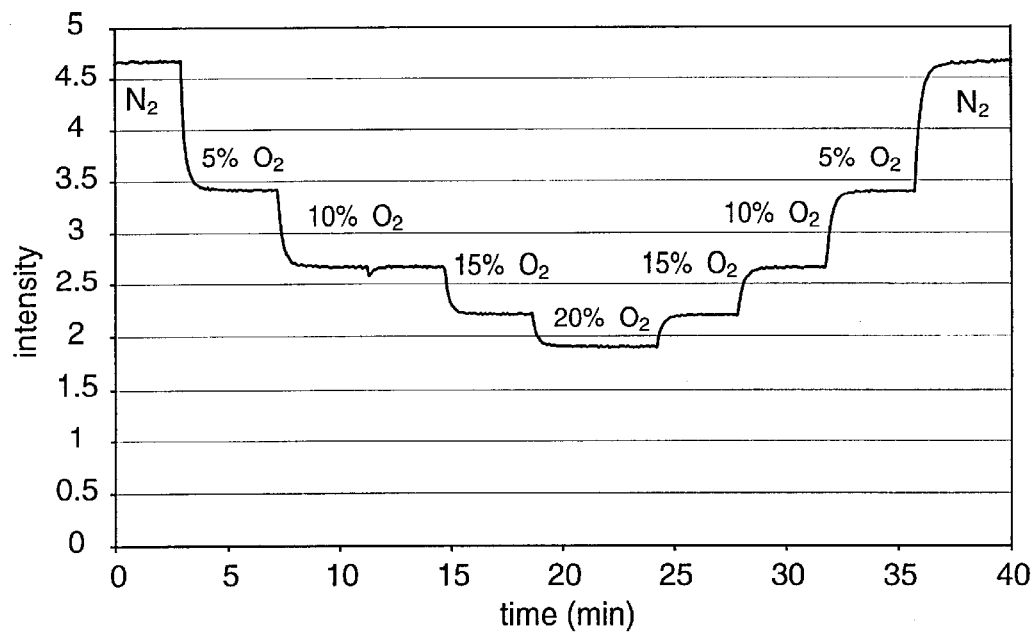
FIG. 9 is a graph showing fluorescence intensity as a function of oxygen partial pressure for sensor film F as measured on the 30 kHz Phase breadboard.
Figure 10:
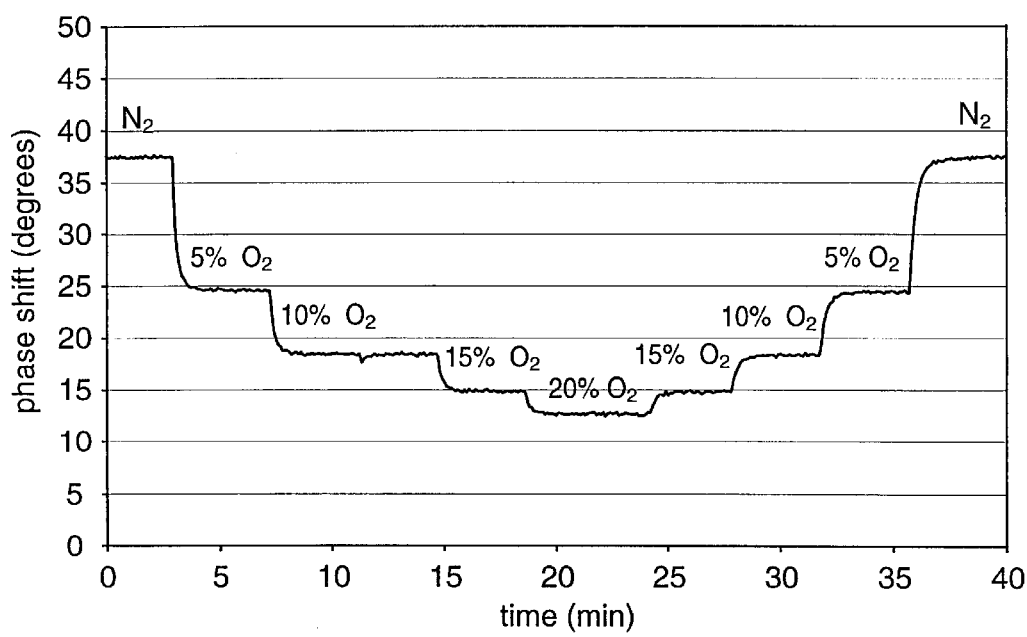
FIG. 10 is a graph showing phase shift as a function of oxygen partial pressure for sensor film F as measured on the 30 kHz Phase breadboard.

FIGS. 9 and 10 show the amplitude and phase shifts obtained for sensor film F (21.4% diphenyl content) as a function of oxygen partial pressure. In this case, the fluorescence intensity drops by only 27% and the phase shift drops by only 34% (or 12.7 degrees) on going from 0% to 5% oxygen. Sensor film F also shows an increased sensitivity at higher oxygen partial pressures, when compared with sensor film A above. For sensor film F, a change from 15% to 20% oxygen produces an additional 5.9% decline in fluorescence intensity and an additional 6.2% decline (or 2.33 degrees) in phase shift.

Figure 11:
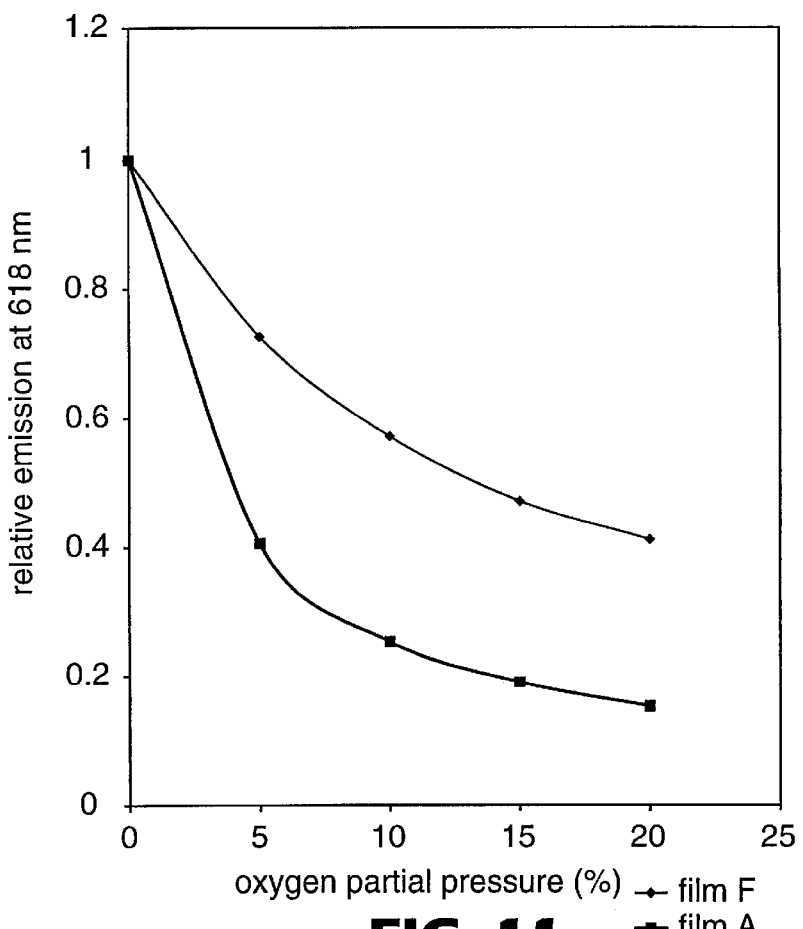
FIG. 11 is a calibration plot illustrating the oxygen dependence of fluorescence quenching of sensor films A and F based on measurement of the amplitude of a modulated 30 kHz carrier signal.

Referring to FIGS. 7 and 9, the amplitudes of the fluorescent emission for sensor films A and F were determined for each of the oxygen partial pressures shown by averaging all the data points on each plateau of the curve. These average values were plotted in FIG. 11. It can be seen from this plot that for oxygen partial pressures around 100 mm Hg (or 13.2% oxygen) that sensor film F has a higher slope than sensor film A and is therefore more sensitive to small changes in oxygen partial pressure in this range.

In certain applications, such as monitoring blood gases in a clinical setting by use of an arterial shunt, it is of value to provide accurate arterial blood gas measurements on an intermittent basis. For a healthy patient, arterial oxygen partial pressures are around 100 mm Hg and must be measured to ±1 mm Hg. In combination with the 30 KHz breadboard, this can be readily achieved with sensor film A, and more preferably with sensor film F.

Figure 12:
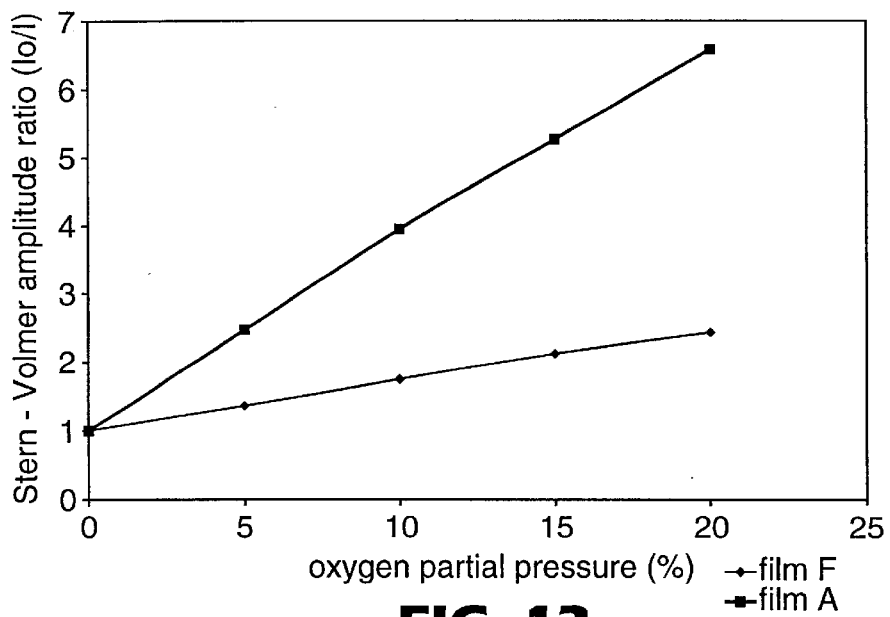
FIG. 12 is a graph illustrating Stern-Volmer plots of the amplitude data from FIG. 11.

FIG. 12 shows Stern-Volmer calibration plots for sensor films A and F, obtained by plotting the ratio of the fluorescence intensity in the absence of oxygen with the corresponding intensities in the presence of various oxygen partial pressures. These plots are essentially linear, consistent with Stern-Volmer quenching kinetics (Equation 1). For sensor films A and F, Stern-Volmer slopes $K_{SV}$ are 0.038 mm$^{-1}$ and 0.0099 mm$^{-1}$ were determined from a least squares regression of the two plots in FIG. 12. For the amplitude precision of 0.1% achieved with our breadboard, corresponding precisions for the oxygen partial pressure can be determined and are given in parenthesis in FIG. 12 for each of the two sensor films.

Referring to FIGS. 8 and 10, the phase shifts of the fluorescent emission for sensor films A and F were determined for each of the oxygen partial pressures shown by averaging all the data points on each plateau of the curve. These average values are plotted in FIG. 13. It can be seen from this plot that for oxygen partial pressures around 100 mm Hg (or 13.2% oxygen) that sensor film F has a higher calibration slope than sensor film A and is therefore more sensitive to small changes in oxygen partial pressure in this range. FIG. 14 shows Stem-Volmer calibration plots for sensor films A and F, obtained by plotting the ratio of tan θ in the absence of oxygen with the corresponding value of tan θ in the presence of various oxygen partial pressures. Note that the Stern-Volmer slopes obtained from the phase data (FIG. 14) are slightly higher than the Stern-Volmer slopes obtained from the raw amplitude data (FIG. 12). This is a result of the fact that the amplitudes measured at 30 kHz are the product of fluorescence intensity and demodulation ratio. To correct for this, the phase shifts were used to estimate the fluorescence lifetime at each oxygen partial pressure. These lifetimes were used to estimate the demodulation ratio at each partial pressure. FIG. 14 also shows Stern-Volmer plots for the amplitude data corrected for the demodulation ratio. These plots are essentially linear and consistent with Stern-Volmer plots achieved using phase detection.

Stability Results

A sensor film was prepared by coating a formulation according to sensor film A onto an m-sol primed Zeonex film and allowing it to thermally cure. A circular disk (ca 4 mm dia) of this material was then cut from the film and glued into the oxygen sensor channel of a System 400 cassette. This cassette was mounted into the System 400 optics head of the 30 kHz phase breadboard. 25 mM sodium phosphate buffer (pH 7.6 and 37.1° C.) was passed through the cassette in a circular flow. The buffer was alternately sparged with nitrogen or air over a 120 hr period while the amplitude and phase of the fluorescent emission of the sensor was monitored.

The breadboard LED was operated at 30 kHz carrier frequency, a burst duration of 0.2 seconds, a repetition rate of 5 sec, and an average output power of 2.5 mW. The irradiated portion of the sensor disk was approximately 2 mm in diameter. Table 4 shows the amplitude and phase shifts obtained at the beginning and the end of the 120 hr experiment.

TABLE 4

Amplitude and Phase Measurements Before and After 120 hrs of Continuous Operation of a Ru based O$_2$ sensor on the 30 kHz phase breadboard.*

|        | I(N2)         | I(air)        | phase(N2)    | Phase(air)     |
|--------|---------------|---------------|--------------|----------------|
| 1 hr   | 1.129 (0.003) | 0.310 (0.002) | 42.38 (0.12) | 17.71 (0.22)   |
| 120 hr | 0.908 (0.005) | 0.260 (0.001) | 42.13 (0.25) | 17.64 (0.24)   |

*numbers in parenthesis represent the standard deviations for the measured quantities in the absence of signal averaging.

The amplitude of the emission signal dropped by 19.5%, but the referenced phase shift changed by only 0.25 degrees under nitrogen and 0.07 degrees under air. Control experiments showed no loss of fluorescence when a second sensor was exposed to the same buffer and flow conditions, but with the LED turned off. This indicates that the decline in the emission is associated with photodegradation of the indicator, not leaching.

Variable Temperature Results

A sensor film was prepared by coating a formulation according to sensor B onto an m-sol primed Zeonex film and allowing it to thermally cure. A circular disk (ca 4 mm dia) of this material was then cut from the film and glued into the oxygen sensor channel of a System 400 cassette. This cassette was mounted into the System 400 optics head of the 30 kHz phase breadboard. 25 mM sodium phosphate buffer (pH 7.6) was passed through the cassette in a circular flow. The buffer was alternately sparged with nitrogen or air while the amplitude and phase of the fluorescent emission of the sensor was monitored on the breadboard. The breadboard LED was operated at 30 kHz carrier frequency, a burst duration of 0.2 seconds, a repetition rate of 5 sec, and an average output power of 2.5 mW.

Figure 15:
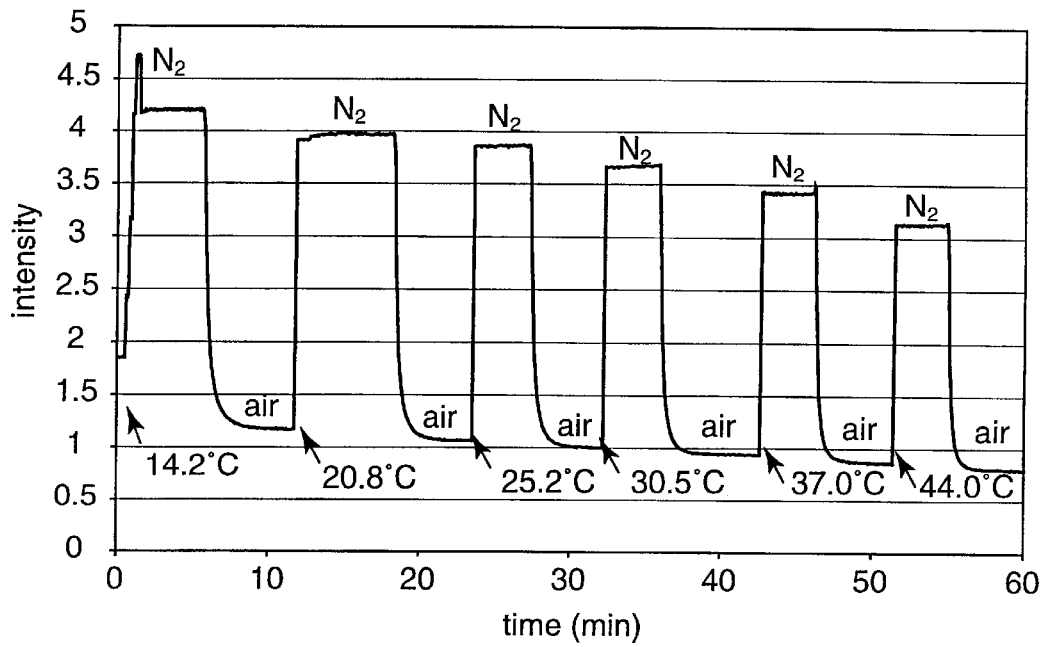
FIG. 15 is a calibration plot of the emission amplitude for sensor film B at various temperatures as the sensor film is alternately exposed to a buffer solution that is equilibrated with nitrogen or air.
Figure 16:
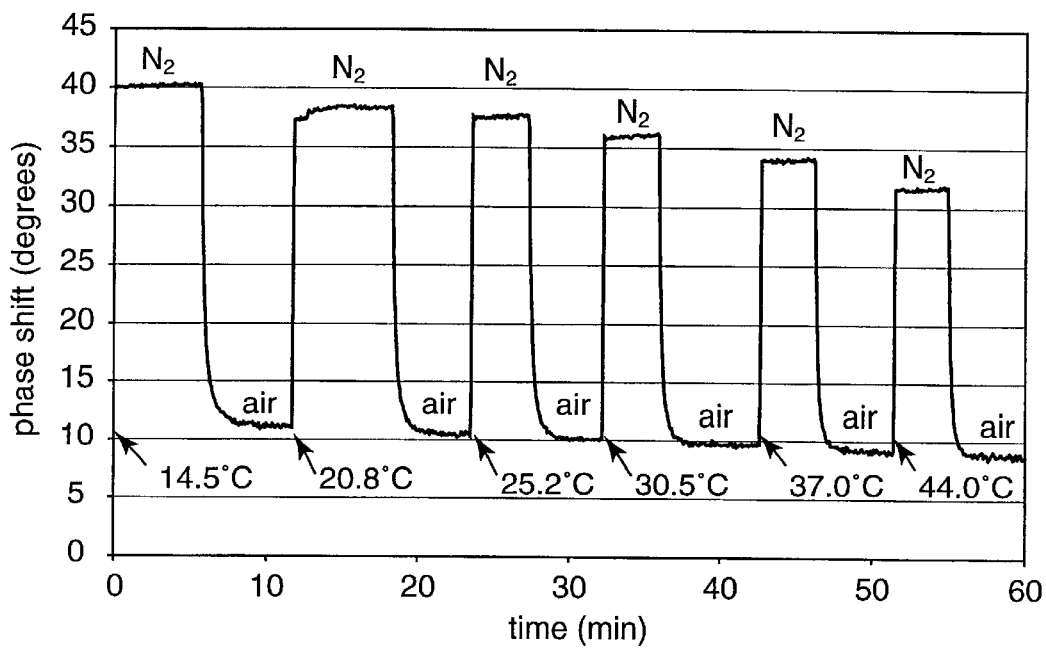
FIG. 16 is a calibration plot of the phase shift for sensor film B at various temperatures as the sensor film is alternately exposed to a buffer solution that is equilibrated with nitrogen or air.

The temperature of the buffer was changed from 14.5, to 20.8, to 25.2, to 0.5, to 37.0 and to 44.0° C. FIG. 15 shows the temperature dependent amplitude changes. FIG. 16 shows the temperature dependent phase shifts. Table 5 gives the averaged amplitudes and phase shifts at each temperature.

TABLE 5

Temperature dependence of the amplitude and phase shift for the oxygen sensors

| Temperature | I(N$_2$) | I(air) | phase(N$_2$) | phase(air) | I(N$_2$)/I(air) | Phase(N$_2$) – phase(air) |
|---|---|---|---|---|---|---|
| 14.5 | 4.2 | 1.17 | 40.2 | 11.2 | 3.589744 | 29 |
| 20.8 | 3.96 | 1.07 | 38.13 | 10.58 | 3.700935 | 27.55 |
| 25.2 | 3.86 | 1 | 37.57 | 10.14 | 3.86 | 27.43 |
| 30.5 | 3.68 | 0.944 | 36.03 | 9.7 | 3.898305 | 26.33 |
| 37 | 3.42 | 0.868 | 34.03 | 9.17 | 3.940092 | 24.86 |
| 44 | 3.13 | 0.799 | 31.6 | 8.7 | 3.917397 | 22.9 |

These values can be incorporated into a lookup table to correct for variations in temperature.

For certain applications such as blood gas monitoring during open heart surgery, it is desirable to be able to measure blood gases over the range of 40–180 mm (5.26% to 23.7% oxygen) and with a precision of ±3 mm (±0.4% oxygen). To meet this specification using sensor film A, the fluorescence intensity must be measured with a precision of ±0.3% [(3.8/5.0)×0.4=0.3]. Correspondingly, the phase shift must be measured with a precision of ±0.07 degrees. These precision requirements could not be achieve with compact optoelectronic devices of the prior art. However, using a combination of our LED phase breadboard optics design and internal referencing as described above, the digital least squares phase and amplitude estimator described above, and the covalently labeled oxygen sensor of this invention, we have exceeded this requirement. Referenced phase shifts remain stable to within ±0.02 degrees and referenced amplitudes remained stable to within ±0.1% for at least 72 hours.

For blood gas monitoring applications, further improvements can be made by reducing the oxygen sensitivity of the sensing element such that the amplitudes and phase shifts change less dramatically below 5% oxygen partial pressure and more dramatically for oxygen partial pressures between 5% and 20%. This was achieved using the formulation of sensor film F.

Example 6

Phase Modulation Oxygen Sensing with a 30 KHz Modulation Frequency

From a detennination of the phase shifts $\theta_o$ at 0% oxygen, it is possible to calculate the fluorescence lifetime of compound 2, $\tau_o$, in each of the sensor films A and F using the formula $$\tan \theta_o = 2\pi f \tau_o$$

In this calculation, f=30 kHz is the modulation frequency. For phase shifts of $\theta_o$=43.81° for sensor film A and $\theta_o$32 37.50° for sensor film F, one can calculate lifetimes of $\tau_o$(A)=5.1 μsec and $\tau_o$(B)=4.1 μsec. This indicates that the fluorescence lifetime of compound 2 is only slightly affected by the polymer host, even though the Stem-Volmer slopes vary significantly.

Figure 13:
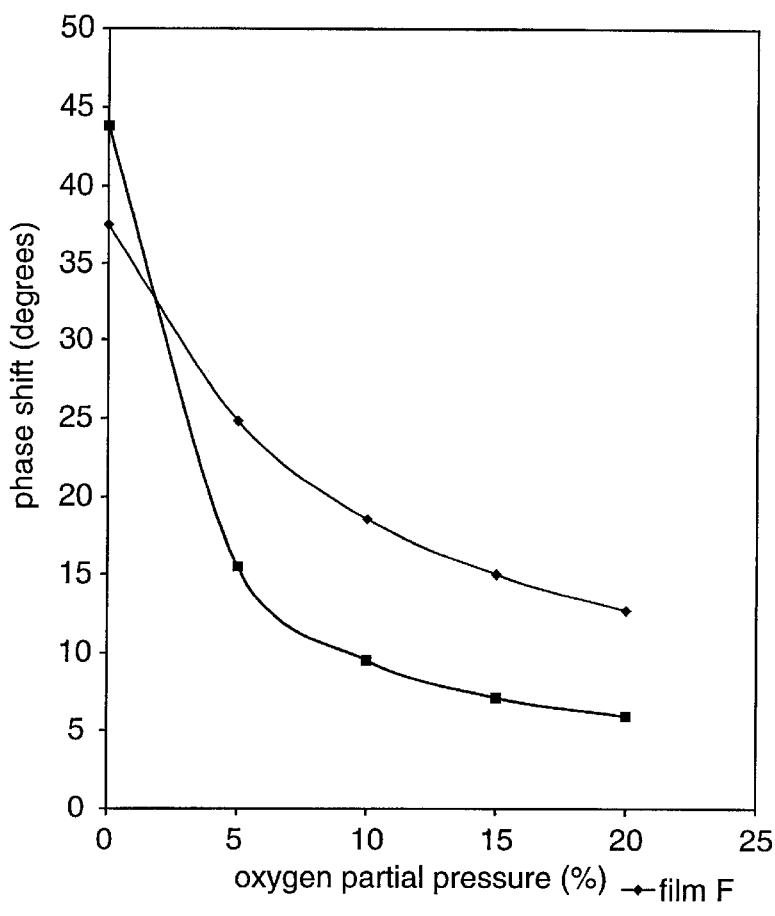
FIG. 13 is a calibration plot illustrating the oxygen dependence of the phase shift of fluorescence from sensor films A and F using a 30 kHz carrier signal.
Figure 14:
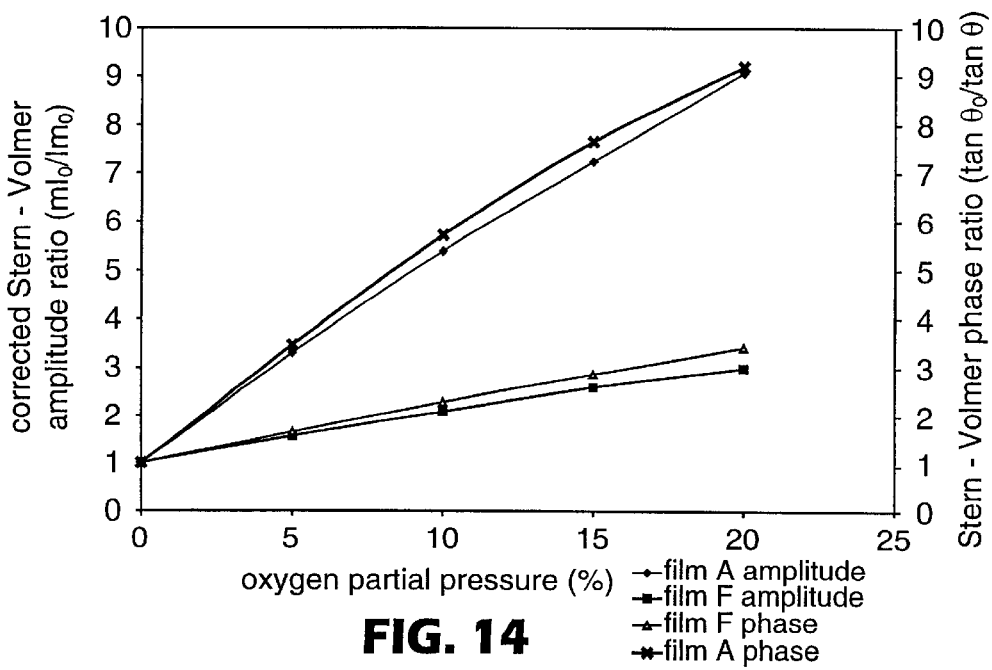
FIG. 14 is a graph illustrating Stern-Volmer plots for sensor films A and F based on (a) measurement of the phase shift and (b) based on measurement of the amplitude corrected for demodulation ratio.

The Stern-Volmer constants derived from FIG. 14 can be combined with the fluorescence lifetimes derived from FIG. 13 to estimate the product a$k_q$=7.4×10$^3$ mm$^{-1}$sec$^{-1}$ for sensor film A and a$k_q$=2.4×10$^3$ mm$^{-1}$ sec$^{-1}$ for sensor film F. These results suggest that the major contribution to the difference in oxygen sensitivity of these two sensors is related to a polymer dependent change in the oxygen solubility, a, or the bimolecular quenching rate constant, $k_q$, in these host polymers.

In phase-modulation fluorescence spectroscopy, the modulation frequency is typically chosen such that ωτ=1 within the range of analyte concentration of interest. This corresponds to a phase angle of near 45 degrees, where a calculation of the lifetime is least sensitive to small errors in the measured phase shift and measured demodulation ratio. For polyaromatic hydrocarbons, $\tau_o$ is generally less than 100 nanosec and phase shift measurements must be made at modulation frequencies of greater that 2 MHz. This generally requires the use of a more complicated heterodyne phase detection method. The advantage of using sensor systems of the present invention is that long fluorescence lifetimes enable phase-modulation detection techniques to be used at low modulations frequencies, such as the 30 kHz frequency used in Example 5. In this situation, the much simpler base-band detection techniques can be used. However, one of the problems with this approach has been that the Stern-Volmer slopes are so high that sensitivity to oxygen partial pressures in the physiological range can be reduced. We have improved on this by using a copolymer of dimethyl and diphenyl siloxane in Sensor film F. This reduces the Stern-Volmer slope by reducing the oxygen solubility in the polymer without affecting the fluorescence lifetime. This allows the sensor system to be used at low modulation frequencies where base-band detection can be employed and phase shifts near 45 degrees can be employed.

Example 7

Selecting Modulation Frequencies

For sensor systems that employ sensor film A, the sensing system can be optimized by increasing the modulation frequency such that the calibration curve is centered near 45 degrees. Using the data obtained at 30 kHz, it is possible to estimate the calibration curves that would be obtained with these sensor systems if the modulation frequencies were increased. To do this, we use the simplifying assumption that $\tan \theta = 2\pi f \tau$. For each of the phase shifts measured at $f_1$=30 kHz, a corresponding phase shift can be estimated at an alternate frequency $f_2$ according to the equation $$\tan \theta_2 = (f_2/f_1) \tan \theta_1$$

Figure 17:
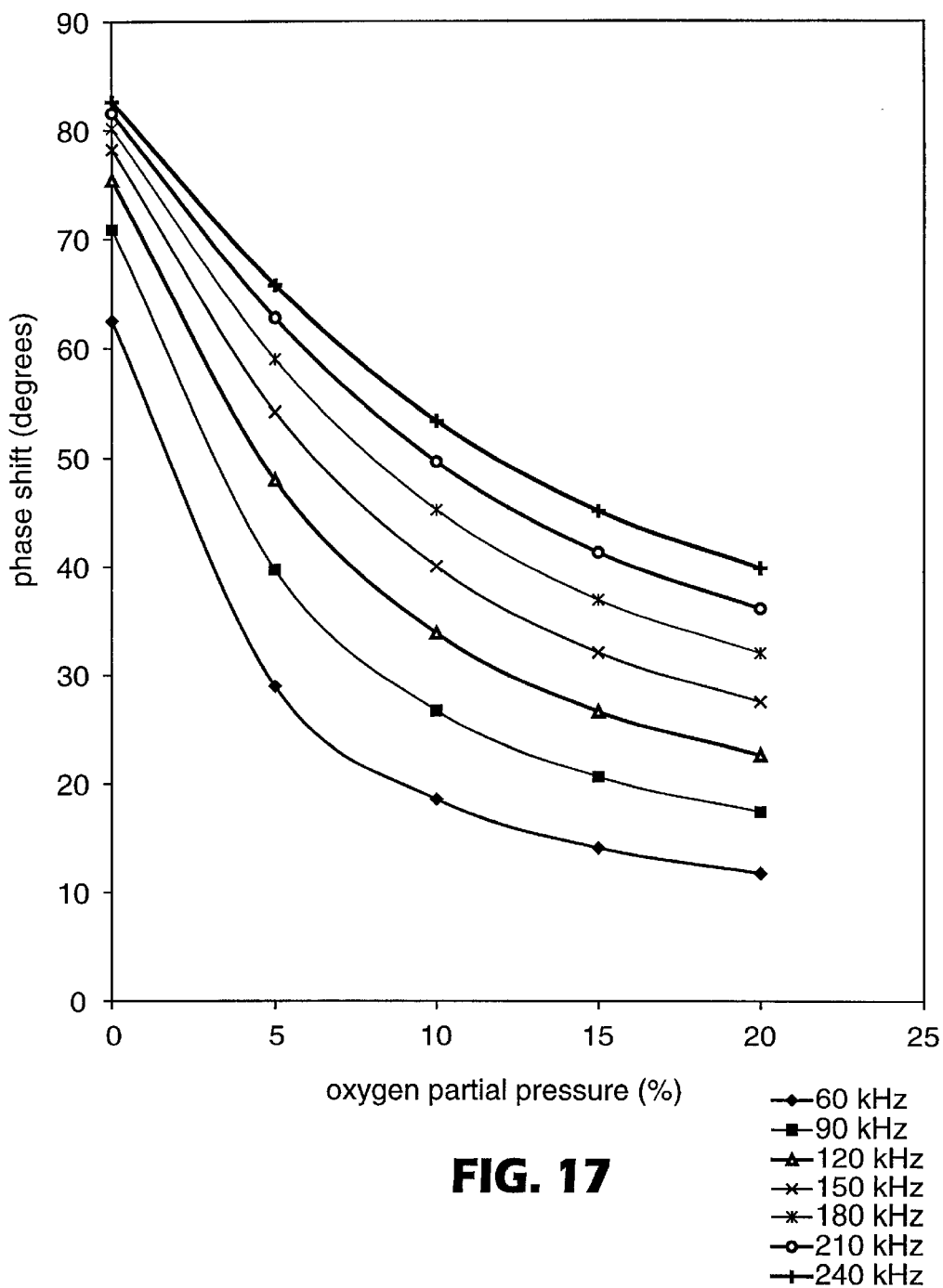
FIG. 17 is a graph illustration of estimated plots of phase shift as a function of oxygen partial pressure for sensor film A as a function of modulation frequency.

FIG. 17 shows the estimated calibration curve expected for sensor film A at several different modulation frequencies ranging from 60–240 kHz. For sensor systems designed to operate in the range of 40–180 mm (5.26% to 23.7% oxygen), operating frequencies of 150 kHz to 210 kHz would provide phase shifts in the range of 30–60 degrees, where the highest precision can be obtained. These modulation frequencies can be implemented using the base-band design.

Importantly, the operation of sensor film A with modulation frequencies near 150 kHz and higher provides an additional attribute first recognized in U.S. Pat. No. 5,462, 879. Under these conditions, the inequality given below holds and calibration slopes become independent of variations in $\tau_o$.

$$[(ak_q[O_2])^2 + \omega^2]\tau_o^2 \gg 1 + 2ak_q\tau_o[O_2]$$

Remembering that the measured $\tau_o$=5.1 μsec, a$k_q$=7.4×10$^3$ mm$^{-1}$sec$^{-1}$ and [O$_2$] varies from 40–180 mm, one obtains a minimum ratio of $\{[(ak_q[O_2])^2 + \omega_2]\tau_o^2\}/(1+2ak_q\tau_o[O_2])$=9.97.

Example 8

150 KHz Breadboard

We have designed circuits that enable implementation of a 150 kHz version of the phase breadboard. This offers an improvement over high frequency phase systems of the prior art that were based on emission from polyaromatic hydrocarbon in polymer hosts such as the dimethylsiloxanes. First, the high frequency phase method can be implemented with the extant sensors at 150 kHz using base band detection, instead of 20 MHz using heterodyne detection for the PAH sensors (see FIG. 16 of U.S. Pat. No. 5,462,879). Second, the high frequency phase method can be operated with the extant sensors at phase shifts that bracket 45 degrees where higher precision can be achieved, instead of at phase shifts above 70 degrees (see FIG. 16 of U.S. Pat. No. 5,462,879) where phase precision is reduced.

The physical set-up of the 150 kHz breadboard is identical to FIG. 4, showing the 30 kHz breadboard.

GaN LEDs from Nichia were amplitude modulated at a 150 kHz carrier frequency, a burst duration of 0.2 seconds, a repetition rate of 5 sec, and an average output power of 2.5 mW. The light was focused, passed through a band-pass excitation filter (450 nm±25 nm; % T=52%; out of band blocking=0.001% T; available from SpectroFilm; Woburn, Mass.), and refocused into a multi-fiber optical excitation cable. At the distal end, the fibers of the excitation cable were randomly bifurcated with fibers from a multi-fiber optical emission cable. The distal end terminated in an optical head adapted to receive a flow through cassette. The optical emission cable returned the modulated fluorescent return to a band-pass emission filter such as is available from SpectroFilm (610±35 nm; % T=64%; out-of-band blocking=0.001% T). The filtered optical output was focused onto the active region of an H5783 photo-sensor module (from Hamamatsu). A small fraction of the excitation fibers were directly routed to the detector assembly and attenuated with a neutral density filter to provide a reference optical signal from the LED.

Using a computer-controlled optical shutter, the photodetector alternately sampled the excitation signal and the fluorescent return signal. This provided optical referencing to correct for fluctuations in the LED output amplitude. In addition, an electronic switch was used to alternately sample the detector photocurrent and a 150 KHz electrical reference signal from the frequency generator. The detector output was directed to a three-stage electronic circuit that converted the photocurrent from the photodiode detector to a voltage. The attenuation and switch stage was used to attenuate a reference electrical signal from the LED drive oscillator and switch between this attenuated reference signal and an unattenuated photosignal.

The transimpedance preamplification stage converts a photocurrent or the reference electrical signal to a voltage using an OPA627 operational amplifier circuit. Some modification of the amplifier circuits shown in FIGS. 2 and 3, which were implemented with a 30 kHz excitation signal, is required. One of ordinary skill in the art will know how to modify the circuits of FIGS. 2 and 3 to operate with a 150 kHz excitation signal.

Figure 18:
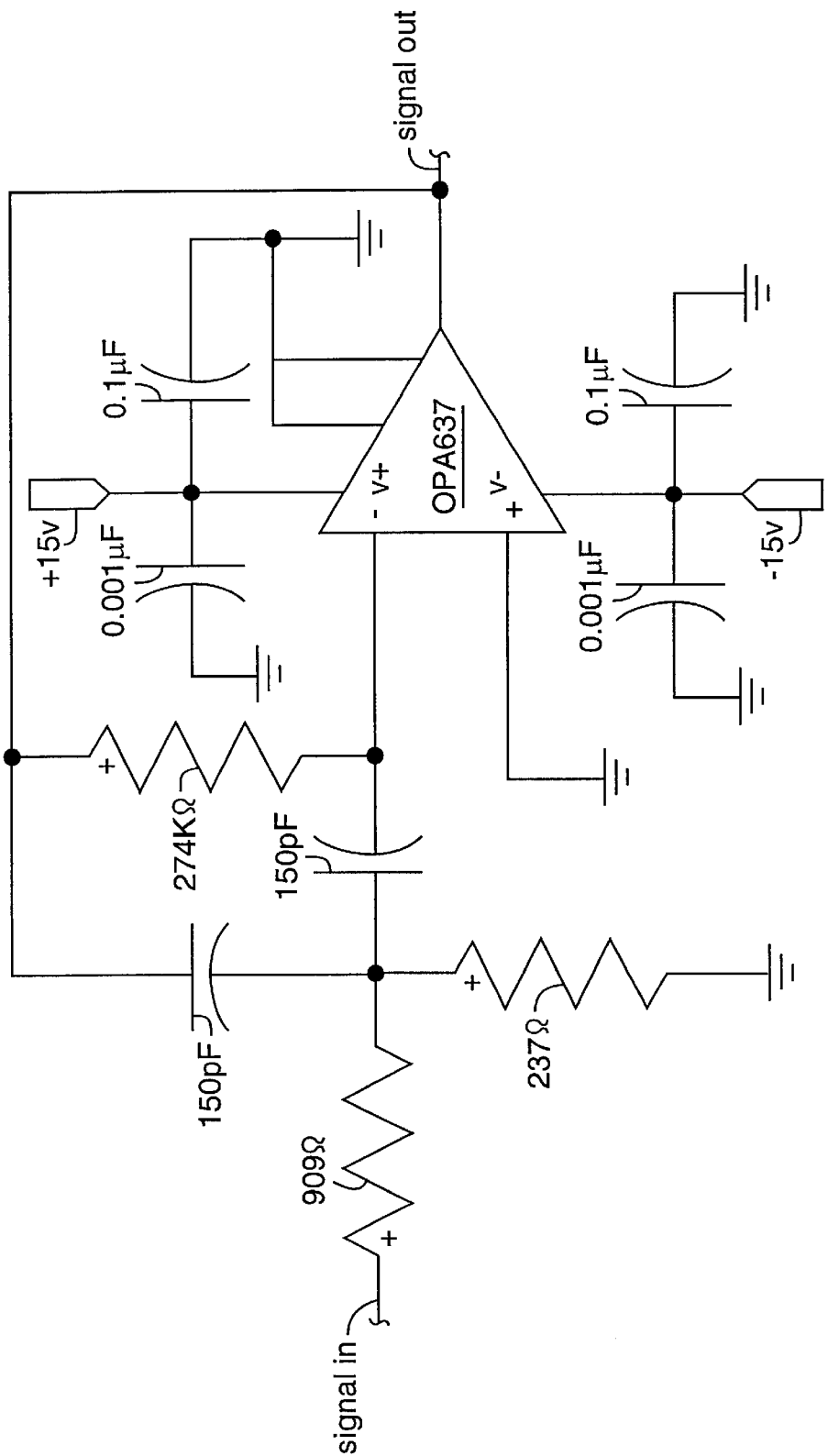
FIG. 18 is a schematic illustration of a multi feedback path amplifier circuit used in one embodiment of a phase-modulation sensor system according to the present invention.

The following stage was a two stage multifeedback path-style bandpass filter using two OPA637 operational amplifiers illustrated in FIG. 18. This stage band-limits the noise power while further amplifying the signal. The center frequency of the three-stage circuitry was about 150 kHz.

The amplified photosignal or reference electrical signal were digitally sampled at 100 kHz and processed using LabVIEW™ virtual instrument software using a least squares estimation of the phase, intensity, and signal-to-noise ratio (SNR). Under these sampling conditions the noise power was further band limited, further increasing the SNR.

In operation, LabVIEW™ software alternately sampled the optical signal from the sample, the optical referencing signal, and the electronic referencing signal. The optical referencing signal corrected for LED fluctuations and the electronic referencing signal corrected for electronic drift associated with temperature, humidity and radio frequency (RF) rectification.

What is claimed is:

1. A composition for sensing oxygen or an oxygen-related analyte in a medium comprising:

a) a solid polymeric matrix which is permeable to oxygen, and b) an indicator covalently bonded to said matrix, wherein said indicator is a luminescent platinum group metal polyaromatic chelate complex capable of having its luminescence quenched by oxygen, said polyaromatic complex comprising three ligands, at least one of which is a bidentate diphenylphenanthroline, said polyaromatic complex being substantially homogeneously distributed throughout the polymeric matrix, said polyaromatic complex being covalently bonded to the matrix through one or more linker arms, wherein each of said one or more linker arms is attached to a phenyl group of the diphenylphenanthroline ligand and to the polymeric matrix.

2. The composition of claim 1 wherein said complex has the formula:

$$M + L_1 L_2 L_3.$$

wherein

$M^+$ is $Ru^{2+}$, $Os^{2+}$; $Ir^{3+}$, or $Rh^{3+}$;

ligands $L_1$ and $L_2$ are identical or different and represent an optionally substituted bidentate phenanthroline or diphenylphenanthroline ligand or an optionally substituted cyclometallated bidentate phenylpyridine or a benzo[h]quinoline ligand;

ligand $L_3$ is a bidentate diphenylphenanthroline ligand substituted by one or more linker arms which covalently link the complex to the matrix material;

where the linker arm comprises a group selected from the group consisting of a covalent bond, O, C(O)O, an optionally substituted methylene group, an optionally substituted carbon chain comprising 2–20 carbon atoms, and combinations thereof, wherein said carbon chain optionally comprises one or more of the following moieties or combinations thereof: an oxygen atom, a nitrogen atom, a sulfur atom, a silicon atom, a heterocyclic group and an aryl group.

3. The composition of claim 1 wherein emission from the complex in said matrix is characterized by one or more fluorescence lifetimes $\tau_o$ above a lowest lifetime $\tau_{oL}=1$ μsec in the absence of oxygen, such that the Stern Volmer constant $K_{SV}$ is greater than 0.006 $mm^{-1}$ and substantially uniform over the range of oxygen partial pressures of 40–180 mm Hg.

4. The composition of claim 1 wherein said polymeric matrix is a silicone-based polymer, and said linker arm is attached to the matrix by a siloxane or silane linkage.

5. The composition of claim 4 wherein said silicone based polymer is derived from precursors having the following formula:

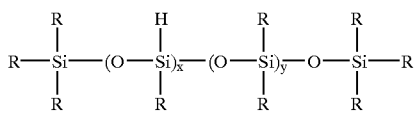

where each of x and y is independently an integer in the range of 1 to about 500 and R is independently selected from the group consisting of H, alkyl, a substituted alkyl, and a phenyl.

6. The composition of claim 4 wherein the silicone based polymer is derived from a precursor having the following formula:

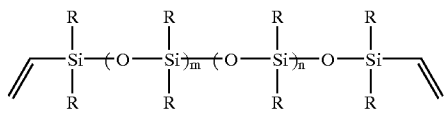

where the sum of m and n is in the range of 100–500, and R is independently selected from the group consisting of alkyl, a substituted alkyl, and a phenyl.

7. The composition of claim 1 wherein the complex is a ruthenium (II) tris[diphenylphenanthroline] complex.

8. The composition of claim 1 wherein the complex has one of the following structures

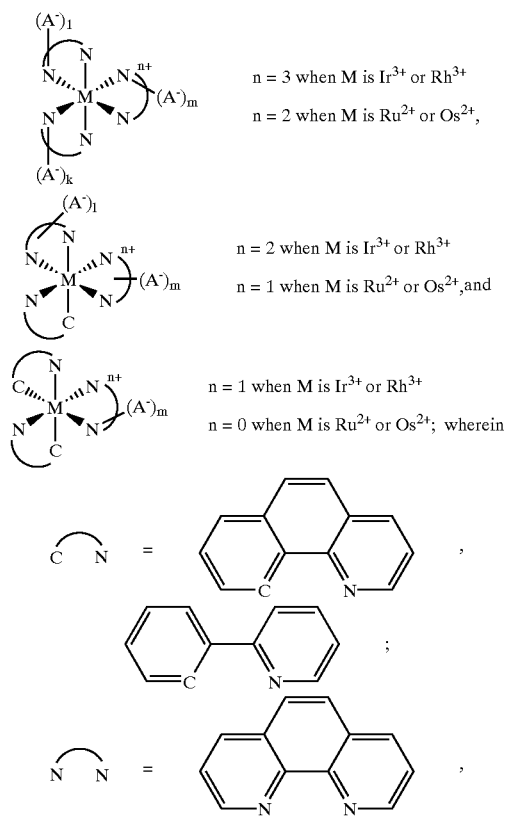

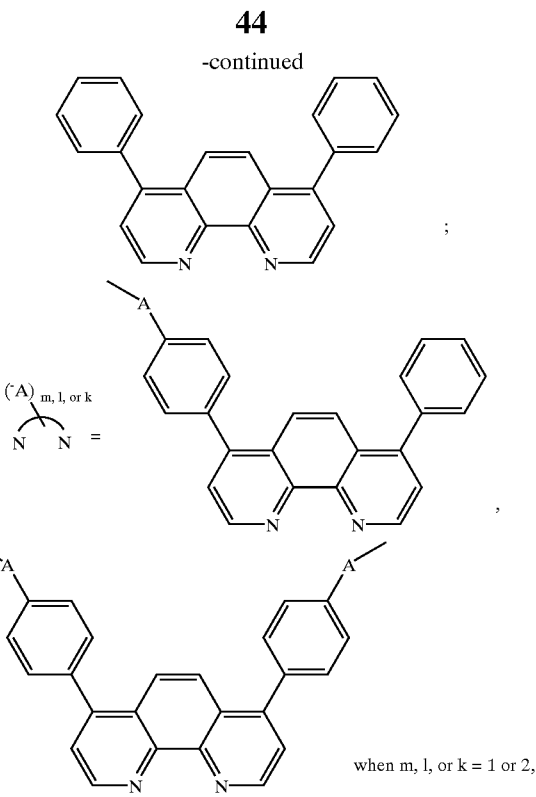

where M is $Ru^{2+}$, $Os^{2+}$; $Ir^{3+}$, or $Rh^{3+}$; A is a linker arm comprising a group selected from the group consisting of a covalent bond, O, C(O)O, an optionally substituted methylene group, an optionally substituted carbon chain comprising 2–20 carbon atoms, and combinations thereof, wherein said carbon chain optionally comprises one or more of the following moieties or combinations thereof: an oxygen atom, a nitrogen atom, a sulfur atom, a silicon atom, a heterocyclic group, and an aryl group; k and l are independently 0, 1, or 2; and m is 1 or 2.

9. A sensing element for measuring the concentration of oxygen or an oxygen-related analyte in a medium, comprising:
(a) the sensing composition of claim 1; and
(b) a substrate for bringing said sensing composition into contact with the medium,
wherein said substrate is made of a material that conducts visible light to and from the sensing composition.

10. The sensing element of claim 9 wherein the substrate is an optical fiber.

11. The sensing element of claim 9 wherein the substrate is a disposable flow-through cassette, and said sensing composition is disposed on a carrier disk which is incorporated into the flow-through cassete.

12. The sensing element of claim 9 wherein said oxygen-related analyte is glucose and said sensing element comprises glucose oxidase.

13. A method for making a composition for sensing oxygen or an oxygen-related analyte in a medium, said method comprising the following steps:
(a) mixing a luminescent platinum group metal polyaromatic chelate complex capable of having its luminescence quenched by oxygen with one or more precursors of a polymeric matrix that is permeable to oxygen, said complex having the following general formula $$M+L_1L_2L_3,$$

wherein $M^+$ is $Ru^{2+}$, $Os^{2+}$; $Ir^{3+}$, or $Rh^{3+}$;

ligands $L_1$ and $L_2$ are identical or different and represent an optionally substituted bidentate phenanthroline or diphenylphenanthroline ligand or an optionally substituted cyclometallated bidentate phenylpyridine or a benzo[h]quinoline ligand;

ligand $L_3$ is a bidentate diphenylphenanthroline ligand substituted by one or more functionalized linker arms capable of covalently linking the complex to the matrix material;

said functionalized linker arm having the structure A–X, where A is comprised of a group selected from the group consisting of a covalent bond, O, C(O)O, an optionally substituted methylene group, an optionally substituted carbon chain comprising 2–20 carbon atoms, and combinations thereof, wherein said carbon chain optionally comprises one or more oxygen atoms, nitrogen atoms, sulfur atoms, silicon atoms, heterocyclic groups, or aryl groups, and where X is selected from the group consisting of a hydroxy, an alkoxy, a halo, a carboxy, an acetoxy, a phenol, a siloxane, and a vinyl group, (b) adding a catalyst to the mixture of step (a), and (c) activating said catalyst to form a polymeric matrix which is covalently bonded to said complex by said linker arm.

14. The method of claim 13 wherein the complex is a salt and comprises a counter anion selected from the group consisting of an organosulfonate, including 3-(trimethylsilyl)-1-propylsulfonate, an organophosphate, tetraphenylborate, $BF_4^-$, $Cl^-$, $Br^-$, $PF_6^-$, $SbF_6^-$, and $ClO_4^-$.

15. A sensor system for determining the concentration of oxygen or an oxygen-related analyte in a medium comprising:

a) the sensing element of claim 9;

b) an excitation assembly which provides the excitation signal to said sensing element;

c) a detector assembly which detects an emitted signal provided by said sensing element; and d) a processor assembly which analyzes the emitted signal in determining the concentration of said analyte in said medium, wherein said sensing element is optically linked to said excitation assembly and said detector assembly, and wherein said detector assembly is in communication with said processor assembly.

16. The sensor system of claim 15 wherein the excitation signal is produced by a light source selected from the group consisting of light emitting diodes, including a GaN light emitting diode, laser diodes, frequency doubled laser diodes, and solid state light sources and wherein the excitation assembly provides a sine wave modulated excitation signal to the sensing composition.

17. The sensor system of claim 16 wherein the sensor system is a phase modulation sensor system and is configured to provide an operating condition such that $[(k_q[O_2])^2+\omega^2]\tau_o^2 >> 1+2k_q\tau_o[O_2]$ and the slope of the relationship between the concentration dependent parameter and analyte concentration is independent of $\tau_o$ variability for all analyte concentrations within the operating range of 40–180 mm Hg and for all lifetimes $\tau_o$ greater than $\tau_{oL}=1$ µsec, and optionally wherein the sensor system is configured to operate at one or more modulation frequencies not to exceed 1 MHz.

18. The sensor system of claim 16 wherein the detector assembly is configured to perform a function selected from the group consisting of (1) sample the modulated excitation signal and a modulated signal emitted by the sensing element, (2) alternately sample the modulated excitation signal and a modulated emitted signal with a single photodetector selected from the group consisting of a photodiode, an avalanche photodiode and a photomultiplier tube, (3) electronically amplify and bandpass filter intensity modulated electrical output signals from the photodetector, and (4) amplify and digitally sample the intensity modulated electrical signal used to modulate the intensity of the light source to correct for fluctuations in the excitation signal amplitude.

19. The sensor system of claim 16 wherein the processor assembly is adapted to use reference signals to determine the extent of the phase shift between the modulated excitation signal and the modulated emission signal, and optionally further wherein the processor assembly in determining the phase shift is adapted and configured to implement a digital least squares algorithm or to implement a Fourier vector analysis.

20. A platinum group metal polyaromatic chelate complex having the following general formula $$M^+L_1L_2L_3$$

wherein $M^+$ is $Ru^{2+}$, $Os^{2+}$, $Ir^{3+}$, or $Rh^{3+}$;

ligands $L_1$ and $L_2$ are identical or different and represent an optionally substituted bidentate diphenylphenanthroline ligand;

ligand $L_3$ is a bidentate diphenylphenanthroline ligand substituted by one or more functionalized linker arms capable of covalently linking the complex to the matrix material;

said functionalized linker arm having the structure A–X, where A or X is comprised of one or more carbon-carbon double bonds or both A and X are comprised of one or more carbon-carbon double bonds.

21. A composition comprising a bidentate diphenylphenanthroline substituted by one or more functionalized linker arms;

said functionalized linker arm having the structure A–X, where A or X is comprised of one or more carbon-carbon double bonds or both A and X are comprised of one or more carbon-carbon double bonds.

* * * * *

UNITED STATES PATENT AND TRADEMARK OFFICE
CERTIFICATE OF CORRECTION

PATENT NO. : 6,664,111 B2
DATED : December 16, 2003
INVENTOR(S) : Bentsen, James G.

It is certified that error appears in the above-identified patent and that said Letters Patent is hereby corrected as shown below:

<u>Column 5,</u>
Line 35, delete "ide", insert in place thereof -- identical or different --;

<u>Column 25,</u>
Line 30, delete "warn", insert in place thereof -- warm --;
Line 47, delete "tunder", insert in place thereof -- under --;

<u>Column 29,</u>
Line 46, delete "the" following "15 minutes", insert in place thereof -- then --;

<u>Column 34,</u>
Line 56, delete "c m", insert in place thereof -- $\omega_m$ --;

<u>Column 35,</u>
Line 1, delete "Nwhich", insert in place thereof -- *N* which --;

<u>Column 39,</u>
Line 46, delete "detennination", insert in place thereof -- determination --;
Line 52, delete "32", insert in place thereof symbol -- = -- (equals);
Line 57, delete "Stem-Volmer", insert in place thereof -- Stern-Volmer --.

Signed and Sealed this

Fifteenth Day of June, 2004

JON W. DUDAS
*Acting Director of the United States Patent and Trademark Office*